US011166464B2

(12) United States Patent
Hart-Cooper et al.

(10) Patent No.: US 11,166,464 B2
(45) Date of Patent: Nov. 9, 2021

(54) SELF-ASSEMBLED ACTIVE AGENTS

(71) Applicants: The United States of America, as represented by the Secretary of Agriculture, Washington, DC (US); METHOD PRODUCTS, PBC, San Francisco, CA (US)

(72) Inventors: William M. Hart-Cooper, Berkeley, CA (US); William J. Orts, Burlingame, CA (US); Kaj Johnson, Sausalito, CA (US); Lauren E. Lynn, Glen Gardner, NJ (US); Diana M. Franqui-Villanueva, Concord, CA (US)

(73) Assignees: The United States of America, as represented by the Secretary of Agriculture, Washington, DC (US); METHOD PRODUCTS, PBC, San Francisco, CA (US)

( * ) Notice: Subject to any disclaimer, the term of this patent is extended or adjusted under 35 U.S.C. 154(b) by 511 days.

(21) Appl. No.: 15/909,421

(22) Filed: Mar. 1, 2018

(65) Prior Publication Data
US 2018/0303100 A1    Oct. 25, 2018

Related U.S. Application Data

(60) Provisional application No. 62/467,324, filed on Mar. 6, 2017.

(51) Int. Cl.
*C07C 279/18*    (2006.01)
*A01N 47/44*    (2006.01)
(Continued)

(52) U.S. Cl.
CPC .............. *A01N 47/44* (2013.01); *A01N 49/00* (2013.01); *A01N 55/08* (2013.01); *C07C 279/18* (2013.01);
(Continued)

(58) Field of Classification Search
None
See application file for complete search history.

(56) References Cited

U.S. PATENT DOCUMENTS

2016/0220510 A1    8/2016    Bullard et al.

FOREIGN PATENT DOCUMENTS

DE    958 832    2/1957

OTHER PUBLICATIONS

Petronilho, Elaine da Conceicao. Design, synthesis, and evaluation of guanylhydrazones as potential inhibitors or reactivators of acetylcholinesterase. Journal of Enzyme Inhibition and Medicinal Chemistry. 31(6), 2016, 1069-1078.*

(Continued)

*Primary Examiner* — Samantha L Shterengarts
(74) *Attorney, Agent, or Firm* — John Fado; Ariel Atkinson

(57) ABSTRACT

A self-assembled active agent may be formed by a process including covalently bonding at least a first component molecule and a second component molecule, the two component molecules displaying synergy such that the effective amount of the self-assembled active agent is lower than the sum of the effective amounts of the first component molecule and the second component molecule. The component molecules may be chosen such that the covalent bonding is reversible, for example through a hydrazone bond between an amine and an aldehyde. The active agent may thus have controllable activity such as an antimicrobial agent, a biocide, an antiviral agent, a preservative, an antifouling agent, a disinfectant, or a sensor agent, such as for a particular molecule or for pH.

5 Claims, 14 Drawing Sheets

(51) Int. Cl.
*A01N 49/00* (2006.01)
*A01N 55/08* (2006.01)
*C07C 281/18* (2006.01)
*C07C 281/16* (2006.01)
*A01N 31/00* (2006.01)

(52) U.S. Cl.
CPC .......... *C07C 281/16* (2013.01); *C07C 281/18* (2013.01); *A01N 31/00* (2013.01); *A01N 2300/00* (2013.01)

(56) References Cited

OTHER PUBLICATIONS

Koskinen, M. Determination of the antileukemic drug mitoguazone and seven other closely related bis(amidinohydrazones) in human blood serum by high-performance liquid chromatography. Journal of Chromatography. 685, 1996, 141-149.*

Nishsimura, T. et al., "Antibacterial Activities of Amidinohydrazones. iii. Antibacterial activities of alkoxybenzaldehde and cinnamaldlehyde amidinohydrazones", Yakugaku Zasshi, (1973), 93(9):1247-1250, see abstract: table 1.

Clustelcean, R. et al., "Aqueous Sulfate Separation by Sequestration of [(SO4)2(H2O)4]4¢ Clusters within Highly Insoluble Imine-Linked Bis-Guanidinium Crystals", Chemistry—A European Journal, (2016), 22(6):1997-2003, See abtract: scheme 1.

Shrestha, S. K. et al., "Bis(N-amidinohydrazones) and N-(amidino)-N0-aryl-bishydrazones: New classes of antibacterial/antifungal agents", Biorganic & Medicinal Chemistry, (2017), 25(1):58-66, (Epub. Oct. 10, 2016), see the whole document.

International Searching Authority, PCT/US2018/020858 for the United States of America, as Represented by the Secretary of Agriculture et al., International Filing Date Mar. 5, 2018.

* cited by examiner

R₁ = H, alkyl
R₂ = H, F, Cl, Br, OR₃, N(R₃)₂, SR₃, B(OH)₂
R₃ = H, alkyl
X = C, N, O, S

Reversible Preservatives from Natural Aldehydes

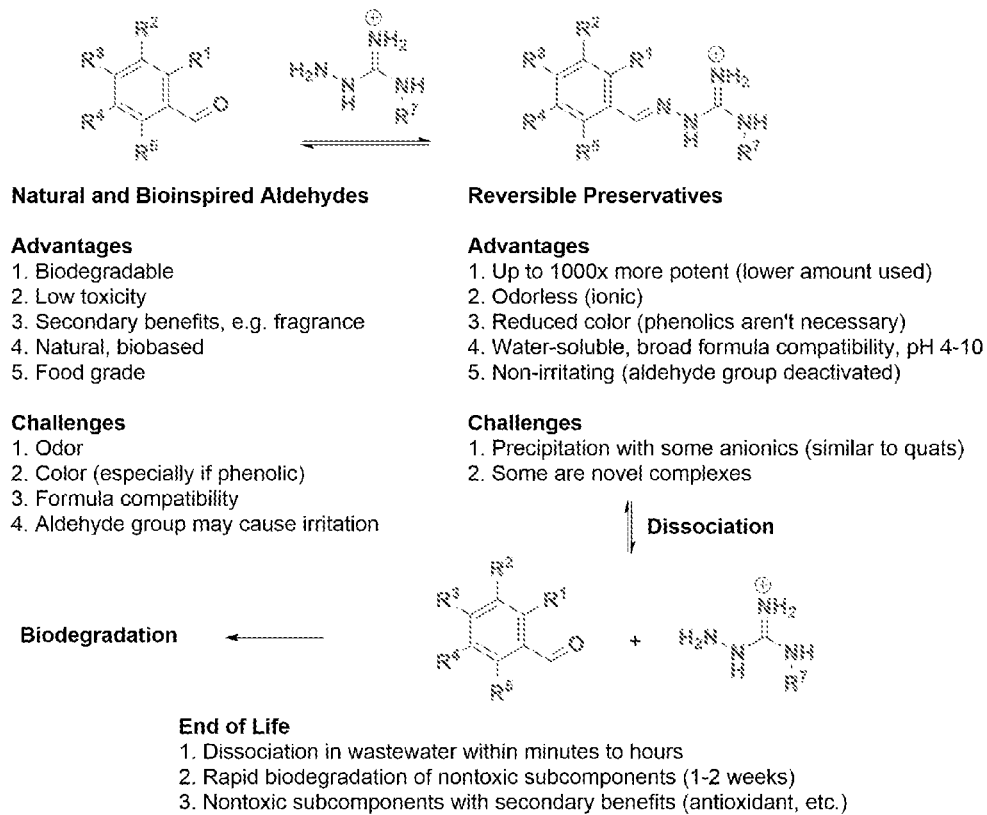

Natural and Bioinspired Aldehydes

Advantages
1. Biodegradable
2. Low toxicity
3. Secondary benefits, e.g. fragrance
4. Natural, biobased
5. Food grade Challenges
1. Odor
2. Color (especially if phenolic)
3. Formula compatibility
4. Aldehyde group may cause irritation

Reversible Preservatives

Advantages
1. Up to 1000x more potent (lower amount used)
2. Odorless (ionic)
3. Reduced color (phenolics aren't necessary)
4. Water-soluble, broad formula compatibility, pH 4-10
5. Non-irritating (aldehyde group deactivated)

Challenges
1. Precipitation with some anionics (similar to quats)
2. Some are novel complexes Dissociation Biodegradation

End of Life
1. Dissociation in wastewater within minutes to hours
2. Rapid biodegradation of nontoxic subcomponents (1-2 weeks)
3. Nontoxic subcomponents with secondary benefits (antioxidant, etc.)

---

Reversible Preservatives as Functional Substitutes for Quats, Guanides

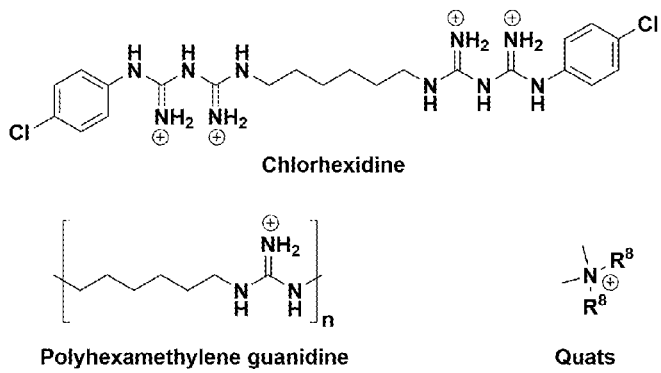

Chlorhexidine

Polyhexamethylene guanidine

Quats

1. Human and environmental, aquatic toxicity
2. Very persistent in the environment
3. Synthetic, not biobased

FIG. 9

SELF-ASSEMBLED ACTIVE AGENTS

REFERENCE TO RELATED APPLICATION

This application claims priority under 35 U.S.C. § 119(e) to U.S. Provisional Ser. No. 62/467,324, which was filed on Mar. 6, 2017, the contents of which are incorporated herein by reference in their entirety.

BACKGROUND OF THE INVENTION

Chemical antimicrobial agents such as antibiotics, antiseptics, disinfectants and preservatives are essential for modern medicine, agriculture and other industries. Despite this importance, chemical antimicrobial agents often exhibit significant toxicity to non-microbial organisms, thereby causing collateral damage to ecosystems and also accelerating the evolution of antimicrobial resistance. The latter two problems may result from a substance's persistence in the environment. The longer a substance persists in the environment, the greater the potential for bioaccumulation and microbial exposure at sub-inhibitory concentrations, the latter of which enables the evolution of antimicrobial resistance. This effect is cause for concern; some estimates predict mortalities from antibiotic resistant infections may surpass those from cancer within several decades. Given the growing hazard of antimicrobial resistance and the damage to the environment caused by persistent chemicals, the development of antimicrobials that are short-lived in the environment is needed.

Hydrazone bond formation has been widely used to construct thermodynamically stable, yet kinetically reversible, covalent molecular complexes that are stable in aqueous solution near neutral pH (Dirksen, et al., Nucleophilic Catalysis of Hydrazone Formation and Transimination: Implications for Dynamic Covalent Chemistry, J. Am. Chem. Soc., 128: 15602-15603 (2006); Rodriguez-Docampo, Z., and S. Otto, Orthogonal or Simultaneous Use of Disulfide and Hydrazone Exchange in Dynamic Covalent Chemistry in Aqueous Solution, Chem. Commun., pages 5301-5303 (2008)). Bond formation and dissociation is dynamic and rapid, often occurring within seconds to minutes at room temperature (King, T. P., et al., Preparation of Protein Conjugates via Intermolecular Hydrazone Linkage, Biochemistry (Mosc.), 25: 5774-5779 (1986); Dirksen, A., and P. E. Dawson, Rapid Oxime and Hydrazone Ligations with Aromatic Aldehydes for Biomolecular Labeling, Bioconjug. Chem., 19: 2543-2548 (2008); and Nguyen, R., and I. Huc, Optimizing the Reversibility of Hydrazone Formation for Dynamic Combinatorial Chemistry, Chem. Commun., pages 942-943 (2003)). These reversible bonds enable pathways for environmental degradation as they dissociate at extreme pH or upon dilution. Custalcean and coworkers employed hydrazone bond formation to construct a class of self-assembled cations that associate strongly with anions (Custelcean, R., et al., Aqueous Sulfate Separation by Crystallization of Sulfate-Water Clusters, Angew. Chem. Int. Ed., 54: 10525-10529 (2015); Custelcean, R., et al., Aqueous Sulfate Separation by Sequestration of $[(SO_4)_2(H_2O)_4]_4{-}$ Clusters within Highly Insoluble Imine-Linked Bis-Guanidinium Crystals, Chem.-Eur. J., 22, 1997-2003 (2016)). These complexes structurally resemble conventional polyguanidines (e.g., chlorhexidine), a class of widely used antimicrobials that are persistent and toxic.

SUMMARY OF THE INVENTION

According to at least one aspect of the invention, a composition may include a compound of the formula:

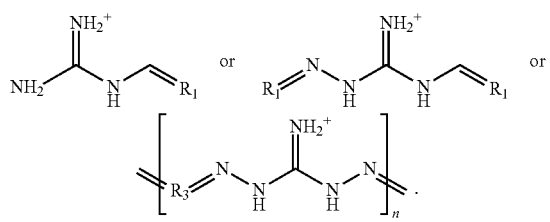

wherein $R_1$ and $R_3$ are, independently, one of a straight chain or branched, saturated or unsaturated aliphatic group, a 5-member ring, or a 6-member ring, $R_1$ and $R_3$ are, independently, optionally substituted one or more times, in the case of either of $R_1$ or $R_3$ being a 6-member ring, the 6-member ring is optionally an aromatic ring, and in the case of either of $R_1$ or $R_3$ having at least one substitution, a first substitution is one of an alcohol group, an aldehyde group, a 5-member ring, a 6-member ring, a halide, a halide-diol, an ether, and a straight or branched, saturated or unsaturated aliphatic group.

According to a further aspect of the invention, the compound may be one of the compounds disclosed in FIG. 5A, FIG. 5B, FIG. 5C and FIG. 5D.

According to at least one aspect of the invention, a composition may include a compound of the formula:

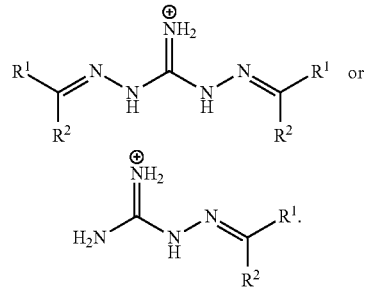

wherein $R^1$ and $R^2$ independently represent:
(1) hydrogen (—H), or
(2) an aliphatic (saturated or unsaturated, straight chain or branched) functional group (e.g., $C_{1-10}$ alkyl) that may be substituted with additional aliphatic groups (e.g. -Me, -Et, where the aliphatic portion ranges from $C_1$ to $C_{10}$), phenolic, —OH groups, ethers (e.g. —OMe, —OEt, where the alkyl portion of the ester ranges from $C_1$ to $C_{10}$), esters (e.g. —CO$_2$Me, —CO$_2$Et, where the alkyl portion of the ester ranges from $C_1$ to $C_{10}$), acids (e.g. boronic, —BO$_2$, or carboxylic, —CO$_2$H), amines and ammoniums (e.g. —NR$^3$R$^4$ or —(NR$^3$R$^4$R$^5$)$^+$), alcohols (e.g. —CH$_2$OH where the alkyl portion of the alcohol ranges from $C_1$ to $C_{10}$), thiol and thioesters (e.g. —SH, —SMe, —SEt, where the alkyl portion of the thioester ranges from $C_1$ to $C_{10}$), halogens (e.g. —Cl, —Br), and/or a 1-2 ring heterocycle that contains O, N and/or S as the heteroatom, such as morpholine, or
(3) an aromatic functional group (e.g., $C_6H_5$ or derivatives wherein one or more —H is substituted with an alkyl (e.g., $C_{1-10}$), with aliphatic groups (e.g. -Me, -Et, where the aliphatic portion ranges from $C_1$ to $C_{10}$), phenolic, —OH groups, ethers (e.g. —OMe, —OEt, where the alkyl portion of the ester ranges from $C_1$ to $C_{10}$), esters (e.g. —CO$_2$Me, —CO$_2$Et, where the alkyl portion of the ester ranges from $C_1$ to $C_{10}$), acids (e.g. boronic, —BO$_2$, or carboxylic, —CO$_2$H), amines and ammoniums (e.g. —NR$^3$R$^4$ or —(NR$^3$R$^4$R$^5$)$^+$), alcohols (e.g. —CH$_2$OH where the alkyl portion of the alcohol ranges from C$_1$ to C$_{10}$), thiol and thioesters (e.g. —SH, —SMe, —SEt, where the alkyl portion of the thioester ranges from C$_1$ to C$_{10}$), halogens (e.g. —Cl, —Br), and/or a 1-2 ring heterocycle that contains O, N and/or S as the heteroatom, such as pyridine or indole; R$^3$, R$^4$ and R$^5$ independently represent a hydrogen of aliphatic (saturated or unsaturated, straight chain or branched, e.g., C$_{1-10}$ alkyl) functional group that may be substituted, for example, with additional aliphatic groups (e.g. -Me, -Et, where the aliphatic portion ranges from C$_1$ to C$_{10}$), —OH groups, ethers (e.g. —OMe, —OEt, where the alkyl portion of the ester ranges from C$_1$ to C$_{10}$), esters (e.g. —CO$_2$Me, —CO$_2$Et, where the alkyl portion of the ester ranges from C$_1$ to C$_{10}$), acids (e.g. boronic, —BO$_2$, or carboxylic, —CO$_2$H), amines and ammoniums alcohols (e.g. —CH$_2$OH where the alkyl portion of the alcohol ranges from C$_1$ to C$_{10}$), thiol and thioesters (e.g. —SH, —SMe, —SEt, where the alkyl portion of the thioester ranges from C$_1$ to C$_{10}$), or halogens (e.g. —Cl, —Br).

According to a further aspect of the invention, the compound may be an active agent.

According to a further aspect of the invention, the active agent may be formed by self-assembly of a first component molecule and a second component molecule.

According to yet a further aspect of the invention, the active agent may have antimicrobial activity.

According to another aspect of the invention, a method for treating a pathogen or microbe may include applying an effective amount of an active agent to a designated area or object, the active agent being the compound described above.

According to a further aspect of the invention, the active agent may be one of the compounds disclosed in FIG. 5A, FIG. 5B, FIG. 5C and FIG. 5D, or FIG. 10 and FIG. 11.

According to another aspect of the invention, a self-assembled active agent may be formed by a process including covalently bonding at least a first component molecule and a second component molecule, and the effective amount of the self-assembled active agent is lower than the sum of the effective amounts of the first component molecule and the second component molecule.

According to a further aspect of the invention, the first component molecule may be an amine and the second component molecule may be an aldehyde.

According to a further aspect of the invention, the first component molecule may be an amine and the second component molecule may be a ketone.

According to a further aspect of the invention, the covalent bonding between the first component molecule and the second component molecule may include the formation of a hydrazone bond.

According to a further aspect of the invention, the first component molecule may have two or more amine functional groups.

According to a further aspect of the invention, the first component molecule may be one of 1,3-diaminoguanidine and aminoguanidine.

According to a further aspect of the invention, the second component molecule may have one or more aldehyde functional groups.

According to a further aspect of the invention, the second component molecule may have three or more aldehyde functional groups.

According to a further aspect of the invention, the second component may be one of glyoxal, glutaraldehyde, benzylaldehyde, phthalaldehyde, terephthalaldehyde, isophthalaldehyde, benzene-1,3,5-tricarboxaldehyde, 2-bromoisophthalaldehyde, 4-tBu-2,6-diformylphenol, 4-Me-2,6-diformylphenol, 3,5-diformyl-2-propoxyphenylboronic acid, 2,5-thiophenedialdehyde, and 2,5-furandialdehyde.

According to another aspect of the invention, a method for killing a microbe may include treating a growth of the microbe with an effective amount of a self-assembled active agent (e.g., a compound disclosed herein that has self-assembled); an effective amount of the self-assembled active agent may be achieved by adding a combination of a pre-determined amount of a first component molecule and a pre-determined amount of a second component molecule, wherein the first component molecule and the second component molecule are capable of self-assembly via the formation of a covalent bond.

According to another aspect of the invention, a method of producing a self-assembled active agent may include combining a first component with a second component, wherein the first component is a molecule with an amine functional group and the second component is a molecule with an aldehyde or a ketone functional group, wherein the first component, the second component, and the combination of the first component and the second component each has a bioactivity, and wherein the bioactivity of the combination of the first component and the second component is greater than the sum of the bioactivity of the first component and the bioactivity of the second component.

According to a further aspect of the invention, the first component and the second component may be capable of self-assembly via the formation of a covalent bond.

According to a further aspect of the invention, the formation of a covalent bond between the first component and the second component may include the formation of a hydrazone bond.

We have developed a new class of antimicrobials (useful against Gram-negative and Gram-positive bacteria, fungi, molds, yeasts, and viruses) based on nontoxic aldehydes and ketones (see the Figures). When treated with a potentiating agent (e.g., aminoguanidine or diaminoguanidine), a reversible covalent complex is formed that surprisingly exhibits selective or narrow- or broad-spectrum antimicrobial activity. Potencies of the resulting complexes are up to 1000 times greater than the sum of their parts. Owing to their surprisingly reversible nature, these complexes are designed to dissociate to nontoxic subcomponents after use. This degradation pathway minimizes the risks of collateral toxicity and antimicrobial resistance.

BRIEF DESCRIPTION OF THE DRAWINGS

Advantages of embodiments of the present invention will be apparent from the following detailed description of the exemplary embodiments. The following detailed description should be considered in conjunction with the accompanying figures in which:

Exemplary

Exemplary

Exemplary

Exemplary

Exemplary

Exemplary

Exemplary

Exemplary

Exemplary FIG. 9 shows synthesis, properties and end-of life for reversible antimicrobials based on benzaldehyde (top) compared to conventional polyguanide and quaternary ammonium (quat) antimicrobials (bottom) as described below.

Exemplary

Exemplary

DETAILED DESCRIPTION OF THE INVENTION

Figure 1:
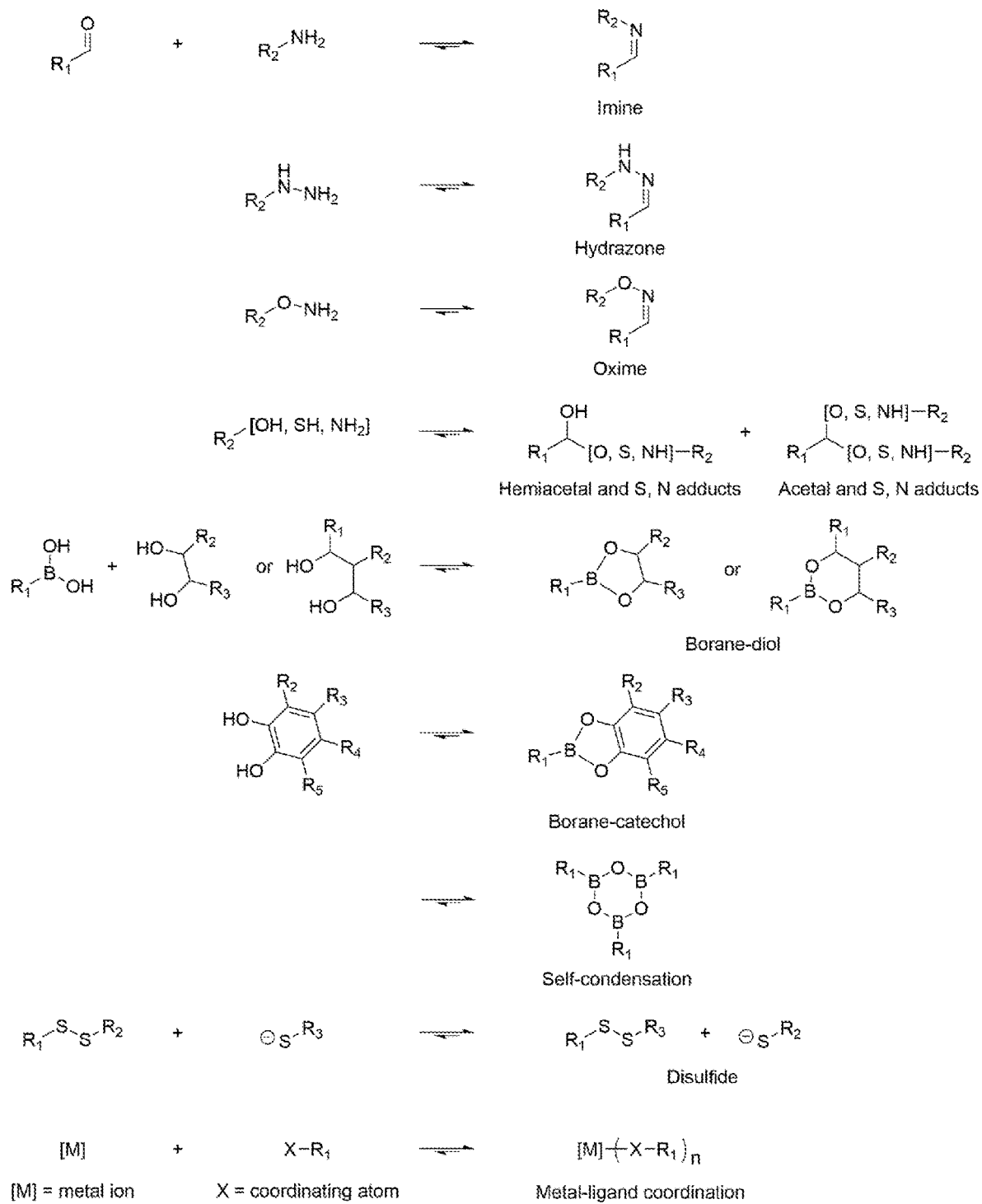
FIG. 1 shows exemplary reversible interactions which may be used to construct self-assembled complexes, including self-assembled active agents, as described below.

Aspects of the invention are disclosed in the following description and related drawings directed to specific embodiments of the invention. Alternate embodiments may be devised without departing from the spirit or the scope of the invention. Additionally, well-known elements of exemplary embodiments of the invention will not be described in detail or will be omitted so as not to obscure the relevant details of the invention. Further, to facilitate an understanding of the description, discussion of several terms used herein follows.

As used herein, the word "exemplary" means "serving as an example, instance or illustration." The embodiments described herein are not limiting, but rather are exemplary only. It should be understood that the described embodiment are not necessarily to be construed as preferred or advantageous over other embodiments. Moreover, the terms "embodiments of the invention", "embodiments" or "invention" do not require that all embodiments of the invention include the discussed feature, advantage, or mode of operation.

Unless defined otherwise, all technical and scientific terms used herein have the same meaning as commonly understood by one of ordinary skill in the art to which the invention belongs. As used herein, the term "about" refers to a quantity, level, value, or amount that varies by as much as 10% to a reference quantity, level, value, or amount. Although any methods and materials similar or equivalent to those described herein can be used in the practice or testing of the present invention, the preferred methods and materials are now described.

Other compounds may be added to the composition provided they do not substantially interfere with the intended activity and efficacy of the composition; whether or not a compound interferes with activity and/or efficacy can be determined, for example, by the procedures utilized below.

The amounts, percentages, and ranges disclosed herein are not meant to be limiting, and increments between the recited amounts, percentages, and ranges are specifically envisioned as part of the invention. All ranges and parameters disclosed herein are understood to encompass any and all subranges subsumed therein, and every number between the endpoints. For example, a stated range of "1 to 10" should be considered to include any and all subranges between (and inclusive of) the minimum value of 1 and the maximum value of 10 including all integer values and decimal values; that is, all subranges beginning with a minimum value of 1 or more, (e.g., 1 to 6.1), and ending with a maximum value of 10 or less, (e.g. 2.3 to 9.4, 3 to 8, 4 to 7), and finally to each number 1, 2, 3, 4, 5, 6, 7, 8, 9, and 10 contained within the range.

"Biological activity" or, in context, "activity" refers to the ability of a compound or composition to (i) prevent the growth of a pathogen or microbe, (ii) inhibit the growth of a pathogen or microbe, or (ii) substantially kill or eliminate a pathogen or microbe population. An active agent is a compound or composition which exhibits substantial biological activity.

The term "treat," "treating," or "treatment," as used herein, refers to the use of a composition to reduce or prevent a condition, symptom, or disease caused by a pathogen or microbe by (i) preventing the growth of the pathogen or microbe, (ii) inhibiting the growth of the pathogen or microbe, or (ii) substantially killing or eliminating the pathogen or microbe. In addition, the term "treat," "treating," or "treatment" may also refer to the use of a composition to kill, reduce the population of, or inhibit the growth of a pest or pest population.

"Microbe" as used herein is synonymous with "microorganism" and may refer to a bacterium, fungus, algae, mold, protozoan, yeast, or other unicellular organism, or a virus.

The term "effective amount" of a compound or property as provided herein is meant such amount as is capable of performing the function of the compound or property for which an effective amount is expressed. As will be pointed out below, the exact amount required will vary from process to process, depending on recognized variables such as the compounds employed and the processing conditions observed. Thus, it is not possible to specify an exact "effective amount." However, an appropriate effective amount may be determined by one of ordinary skill in the art using only routine experimentation.

As used herein, "analog" or "chemical variant" of a compound refers to a structural analog of the identified compound having a similar structure and similar activity.

Objects treated by the methods described herein include surfaces. Objects treated by the methods described herein also include foods and beverages. Foods and beverages treated by the methods described herein include meat, poultry, seafood, eggs, nuts, fruits and vegetables. Particularly included are apples, melons, apricots, peaches, pears, artichokes, beans, bell peppers, carrots, celery, tomato, lettuce, and spinach. Foods particularly include fresh-cut produce (e.g., fruits and vegetables) which is produce that has been, for example, peeled, cut, sliced, or shredded. The fresh-cut produce may be subsequently made into juice, or dried or dehydrated or frozen by methods known in the art. Objects treated by the methods described herein also include a surface, such as a kitchen countertop.

Contacting or exposing objects with the antimicrobial composition described herein (to reduce and/or kill bacteria) may occur by conventional methods such as spraying or dipping or immersion wherein the object is in contact with the antimicrobial solution for a certain period of time (e.g., about 120 seconds).

Unless otherwise indicated, all numbers expressing quantities of ingredients, properties such as molecular weight, reaction conditions (e.g., reaction time, temperature), percentages and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. As used herein, the term "about" refers to a quantity, level, value, or amount that varies by as much as 10% to a reference quantity, level, value, or amount.

The term "consisting essentially of" excludes additional method steps or composition components that substantially interfere with the intended activity of the method or composition, and can be readily determined by those skilled in the art (for example, from a consideration of this specification or practice of the invention disclosed herein).

All of the references cited herein, including U.S. Patents and U.S. Patent Application Publications, are incorporated by reference in their entirety.

A wide range of application rates of the compositions may be suitable in accordance with the present methods. Those working in this field would of course be readily able to determine in an empirical manner the optimum rates of application for any given combination of target microorganisms to be killed or eliminated. The amount of composition used will be at least an effective amount to reduce and/or kill microorganisms. The term "effective microorganisms killing amount" as used herein, means the minimum amount of composition needed to reduce and/or kill the number of microorganisms on or in an object or area (e.g., soil, structures, plants, or agricultural commodities such as grain or wood). Of course, the precise amount of the composition needed will vary in accordance with the particular composition used; the type of object to be treated; the number of days of effectiveness needed; and the environment in which the object is located. The precise amount of the composition can easily be determined by one skilled in the art given the teaching of this application. Other compounds may be added to the composition provided they do not substantially interfere with the intended activity of the composition; whether or not a compound interferes with activity can be determined, for example, by the procedures described below.

The optional carrier may be, for example, agronomically or physiologically or pharmaceutically acceptable carriers known in the art. The carrier component can be a liquid or a solid material. The term "carrier" as used herein includes carrier materials such as those described below. As is known in the art, the vehicle or carrier to be used refers to a substrate such as a mineral oil, paraffin, silicon oil, water, membrane, sachets, disks, rope, vials, tubes, septa, resin, hollow fiber, microcapsule, cigarette filter, gel, natural and/or synthetic polymers, elastomers or the like. All of these substrates have been used to control and release an effective amount of a composition containing the compounds disclosed herein in general and are well known in the art. Suitable carriers are well-known in the art and are selected in accordance with the ultimate application of interest. Agronomically acceptable substances include aqueous solutions, glycols, alcohols, ketones, esters, hydrocarbons halogenated hydrocarbons, polyvinyl chloride; in addition, solid carriers such as clays, laminates, cellulosic and rubber matrices and synthetic polymer matrices, or the like.

"Optional" or "optionally" means that the subsequently described event or circumstance may or may not occur, and that the description includes instances in which said event or circumstance occurs and instances where it does not. For example, the phrase "optionally comprising a known antimicrobial" means that the composition may or may not contain a known antimicrobial and that this description includes compositions that contain and do not contain a known antimicrobial. Also, by example, the phrase "optionally adding a known antimicrobial" means that the method may or may not involve adding a known antimicrobial and that this description includes methods that involve and do not involve adding a known antimicrobial.

Compositions containing one or more (e.g., two) of the compounds described herein may contain one specific compound or may not contain that specific compound. For example, a composition may contain

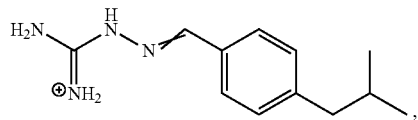 [SMILES: CC(C)Cc1ccc(C=NNC(N)=[NH2+])cc1]

, or the composition may not contain

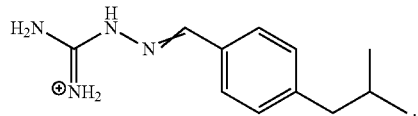 [SMILES: CC(C)Cc1ccc(C=NNC(N)=[NH2+])cc1]

.

The invention illustratively disclosed herein suitably may be practiced in the absence of any element (e.g., method steps or composition components) which is not specifically disclosed herein. Further, the invention described herein may include any one or more of the listed active agents described herein, and in the case of the invention including a single active agent, any other active agent may be optionally excluded.

According to at least one embodiment, self-assembled active agents may be produced using known processes. A self-assembled active agent may be the result of the assembly of two or more components. For example, the self-assembled active agent may be a complex formed by the covalent bonding of two or more component molecules. The self-assembly may occur under a variety of conditions, depending on the desired application. According to at least some embodiments, the self-assembly occurs at room temperature in an aqueous medium. Further, a controlling factor for self-assembly may be concentration of the self-assembled active agent and/or components. For example, in the case where the active agent is sufficiently diluted, the assembly may reverse, and the active agent may break apart into its separate components. The self-assembled active agent may be in the form of an individual molecule, consisting of as little as two components. Alternatively, the self-assembled active agent may be an oligomer or a polymer.

The active agent may have one or more activities. For example, the active agent may be an antimicrobial agent, such as an antibacterial agent. The active agent may also be a biocide such as an herbicide, a pesticide, or an antiviral agent. Additionally or alternatively the active agent may be a preservative, an antifouling agent, or a disinfectant. In the case of the active agent being active against a microbe, bacterium, or virus, the active agent may be termed as having bioactivity. The active agent may also be a sensor agent, such as for a particular molecule or for pH.

The bioactivity of a compound or active agent means the strength of the compound or active agent to kill, treat, reduce the number of, or inhibit growth of a microbe or other biological entity. For example, in the case of inhibition of growth of an organism, bioactivity is inversely proportional to the minimum concentration needed to inhibit the growth of the organism. The bioactivity of a compound or active agent also means the strength of the compound or active agent to remove a microbe or other biological entity depending on the carrier system such as a gel or encapsulating matrix; also the compound or active agent may be a cationic surfactant which can "sweep away" microbes from surfaces.

The components of the active agent may be benign and/or biodegradable compounds. Exemplary components which may be used in an active agent may be amines, aldehydes, and/or ketones. For the purposes of this disclosure, an aldehyde is a molecule with at least one aldehyde functional group, a ketone is a molecule with at least one ketone functional group, and an amine is a molecule with at least one amine functional group. In the case of an amine and an aldehyde being two components to form an active agent, the self-assembly may be achieved via dehydration synthesis. The active agent may thus be formed via a covalent bond, such as a hydrazone bond. Exemplary amines for a component in an active agent may include 1,3-diaminoguanidine and aminoguanidine. Exemplary aldehydes for a component in an active agent may include glyoxal, glutaraldehyde, benzylaldehyde, phthalaldehyde, terephthalaldehyde, isophthalaldehyde, benzene-1,3,5-tricarboxaldehyde, 2-bromoisophthalaldehyde, 4-tBu-2,6-diformylphenol, 4-Me-2,6-diformylphenol, 3,5-diformyl-2-propoxyphenylboronic acid, 2,5-thiophenedialdehyde, and 2,5-furandialdehyde. The active agent may alternatively be formed via an oxime bond, a boronic acid adduct, or any other suitable reversible bond scheme. Exemplary reversible interactions which may be used to construct self-assembled complexes, including self-assembled active agents, are shown in FIG. 1 (adapted from DOI: 10.1002/anie.201610372 and references therein).

Figure 2:
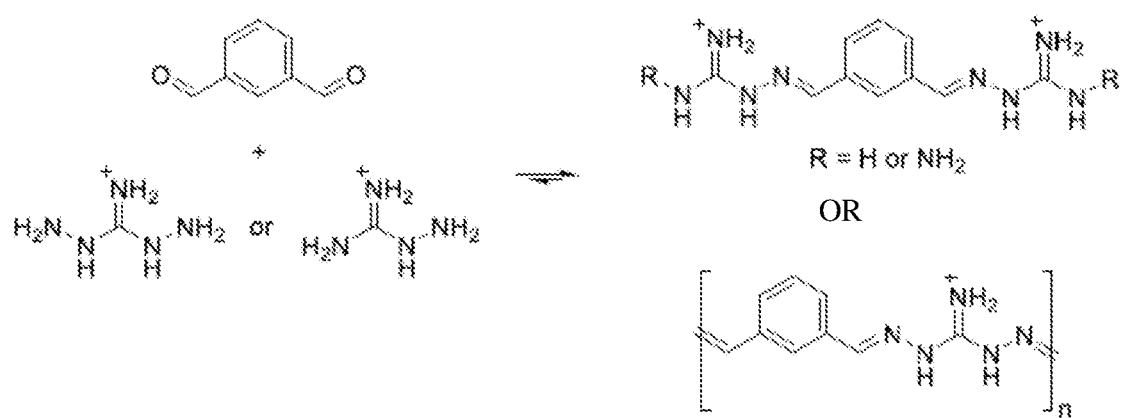
FIG. 2 shows an exemplary scheme for the self-assembly of an active agent using a hydrazone bond through the combination of isophthalaldehyde with either aminoguanidine or 1,3-diaminoguanidine as described below.
Figure 8:
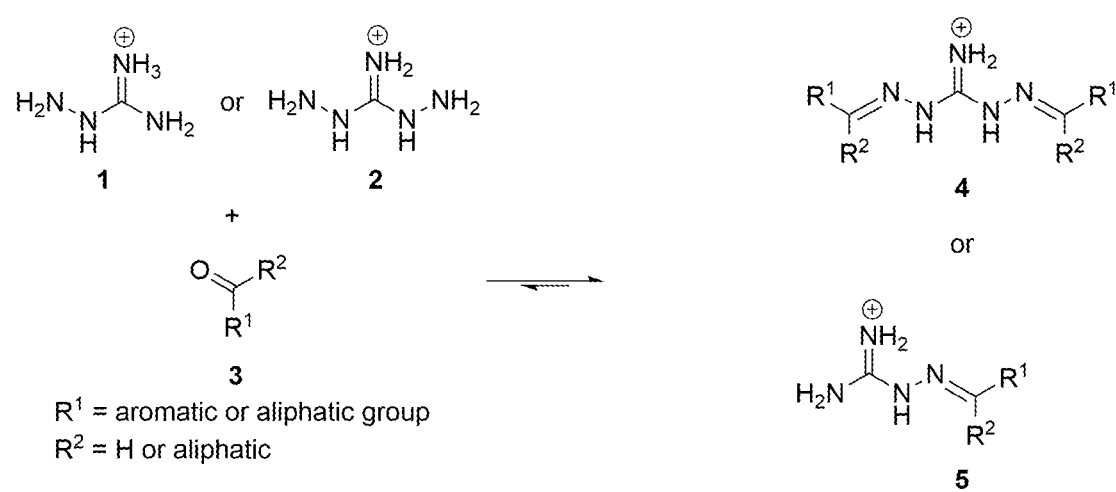
FIG. 8 shows a general scheme describing the formation of 2:1 (4) and 1:1 (5) adducts of mono-aldehydes or ketones with diaminoguanidine (2) or aminoguanidine (1) as described below.
Figure 10:
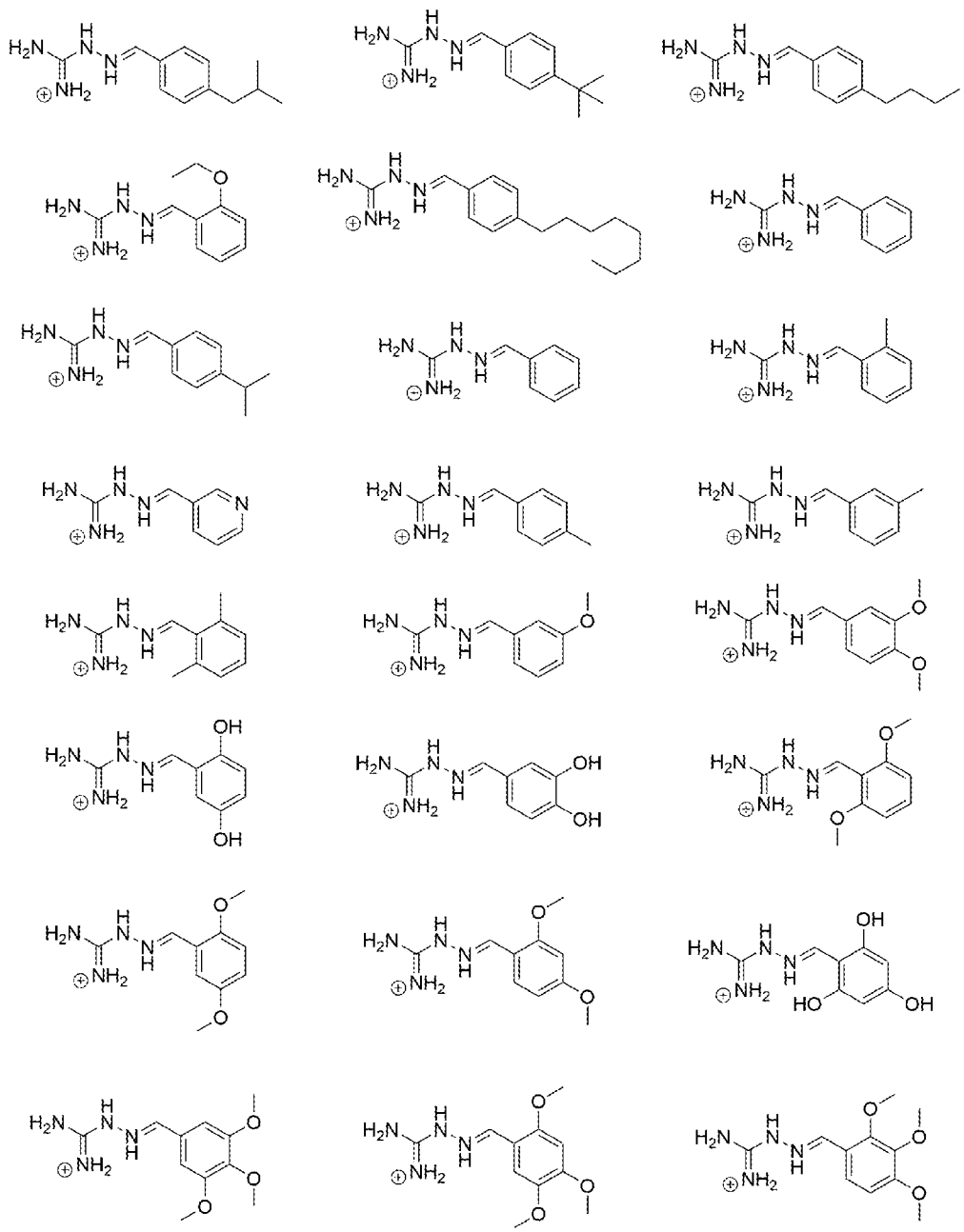
FIG. 10 shows examples of the structures of reversible antimicrobials.
Figure 11:
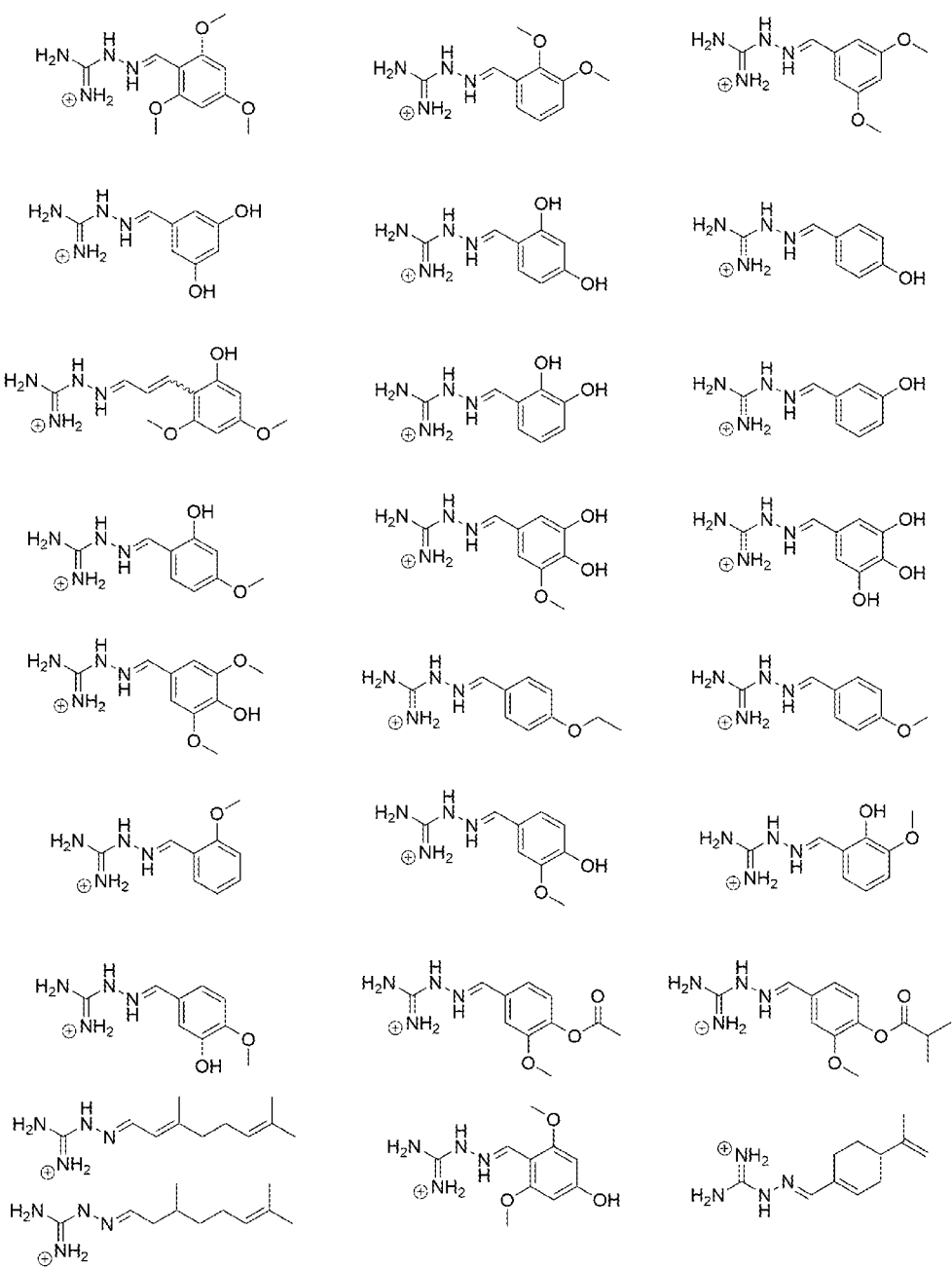
FIG. 11 shows additional examples of the structures of reversible antimicrobials.

An exemplary scheme for the self-assembly of an active agent using a hydrazone bond is shown in FIG. 2 and FIG. 8.

One general procedure for preparation of the antimicrobials (e.g., FIG. 8) is by treating an aldehyde (e.g., 20 mg) or ketone (e.g., 20 mg) with aminoguanidine HCl stock solution (e.g., 180 mg; 37 wt % aminoguanidine HCl in dH$_2$O) or diaminoguanidine. Reactions proceed within seconds but were typically heated for at least about 30 min at about 70° C. to ensure completion. Reactions can be typically run at about 20° to about 70° C. for about 1 minute to about 48 h; lower and higher temperatures also afford the same complexes, albeit at different rates. Typically reactions were run at neutral pH; lower and higher pH affords the same complexes at different rates and purity.

Complexes were constructed from non-toxic aldehydes or ketones and aminoguanidine or diaminoguanidine subcomponents through a dynamic covalent hydrazone linkage (typical reaction conditions: at least about 30 minutes at about 70° C. and about neutral pH). This reversible bond dissociates on the order of seconds to hours when exposed to dilution, changes in pH, temperature, or chemical treatment (e.g., hydrazine or hydroxylamine). Hydrazone bond reversibility is well documented in the scientific literature (Nguyen, R., and I. Huc, Chem. Commun., 8: 942-943 (2003)). Association constants for hydrazone bonds (1:1 hydrazine to aldehyde) in water are typically $10^5$-$10^7$ M$^{-1}$. An association constant of $10^6$ M$^{-1}$ would be >99% complex as a 1 wt % solution, and dissociate ~94% to its subcomponents upon dilution of a 1 L product in a 25-meter swimming pool (375,000 Liters). By providing a novel degradation pathway through dissociation, reversible antimicrobials are produced. Reversible and "controllable" antimicrobial agents are put forward as a way to limit the development of collateral antimicrobial resistance and toxicity through environmental persistence. The general advantage of these microbial agents is that they are active when present in their complexed state and can thus substitute for toxic, nonrenewable antiseptics, disinfectants, and preservatives that are used so prevalently in many consumer/medical products. However, when antimicrobial activity is no longer needed, these active complexes can be de-activated via dissociation, for example though changes in concentration, pH, temperature, or salt concentration.

Although mechanistic investigations are ongoing, without being bound by theory these antimicrobials are envisioned to inhibit microbial growth through multiple mechanisms (e.g., membrane disruption, inhibition of oxidative phosphorylation similar to Robenidine, etc.). Minimum inhibitory concentrations for several complexes were as low as 6-70 ppm for example against resilient strains of Pseudomonas aeruginosa and Aspergillus brasiliensis. This high degree of potency is comparable to conventional, market-leading antibiotics.

Aldehyde and ketone components used to produce the novel antimicrobials may be agriculturally derived (e.g., benzaldehyde, cuminaldehyde, citral from Prunus, cumin and lemongrass-based feedstocks), which could create a novel market for these green product substances. In addition, plant extracts, oils, flavors or fragrances can be used to produce the novel antimicrobials. The antimicrobial complexes themselves may find use as preservatives that would minimize food and water waste. These substances may also be used as antimicrobials, antibiotics, antiparasitics, repellents and pesticides (e.g. against insects), and herbicides and could replace current synthetic chemicals which are generally more toxic and contribute to microbial and pest resistance. These substances could substitute for current pesticides, adjuvants/boosters, anti-biofilm actives, probiotics, disinfectants, antiseptics, antibiotics (topical and oral), and preservatives. These antimicrobials may also be delivered through incorporation of the complex or a subcomponent in packaging. The antimicrobials could be used to coat or be incorporated into bottles, packaging, films, transfer lines/tubing, in process—cleaning tanks, pump surfaces etc.

One big advantage of these antimicrobials is that they exhibit a limited post-use lifetime, thus minimizing opportunities for sub-inhibitory microbial exposure and resulting in development of antimicrobial resistance. Thus antibiotics currently used for agriculture may be replaced by these inexpensive, non-toxic, biobased, and reversible antimicrobials.

To summarize the advantages of this system more directly, in normal use of the consumer product the product would provide maximum efficacy when the complex is together, likely, for example, when both components are at a high concentration. Thus, it is active when needed. However, after use, when efficacy is no long needed and the molecules are being washed down the drain, for example, the complex would naturally and immediately become diluted, whereby the separate molecules are benign and represent little risk to the environment. In the case of agriculture (e.g., when acting as a miticide, pest control, or food preservative), the net effect in almost all imaginable applications is that the complex would become immediately benign after use. It should be noted that the complex could be used in food or feed supplements which lose efficacy in the stomach or soon after digestion.

Reversible antimicrobials, such as those described herein, are relatively safe and benign, and thus would displace many of the current antimicrobials being banned or heavily scrutinized by regulatory agencies and consumers. In cases where current biocides are being heavily regulated, reversible analogues could completely substitute for these products by offering the novel advantage of controlled or predictable dissociation.

While this invention may be embodied in many different forms, there are described in detail herein specific preferred embodiments of the invention. The present disclosure is an exemplification of the principles of the invention and is not intended to limit the invention to the particular embodiments illustrated. Furthermore, the invention encompasses any possible combination of some or all of the various embodiments and characteristics described herein and/or incorporated herein. In addition the invention encompasses any possible combination that also specifically excludes any one or some of the various embodiments and characteristics described herein and/or incorporated herein.

The following examples are intended only to further illustrate the invention and are not intended to limit the scope of the invention as defined by the claims.

EXAMPLES

Antimicrobial Agents: Self-assembled active agents were created using the components shown in Table 1.

Figure 3:
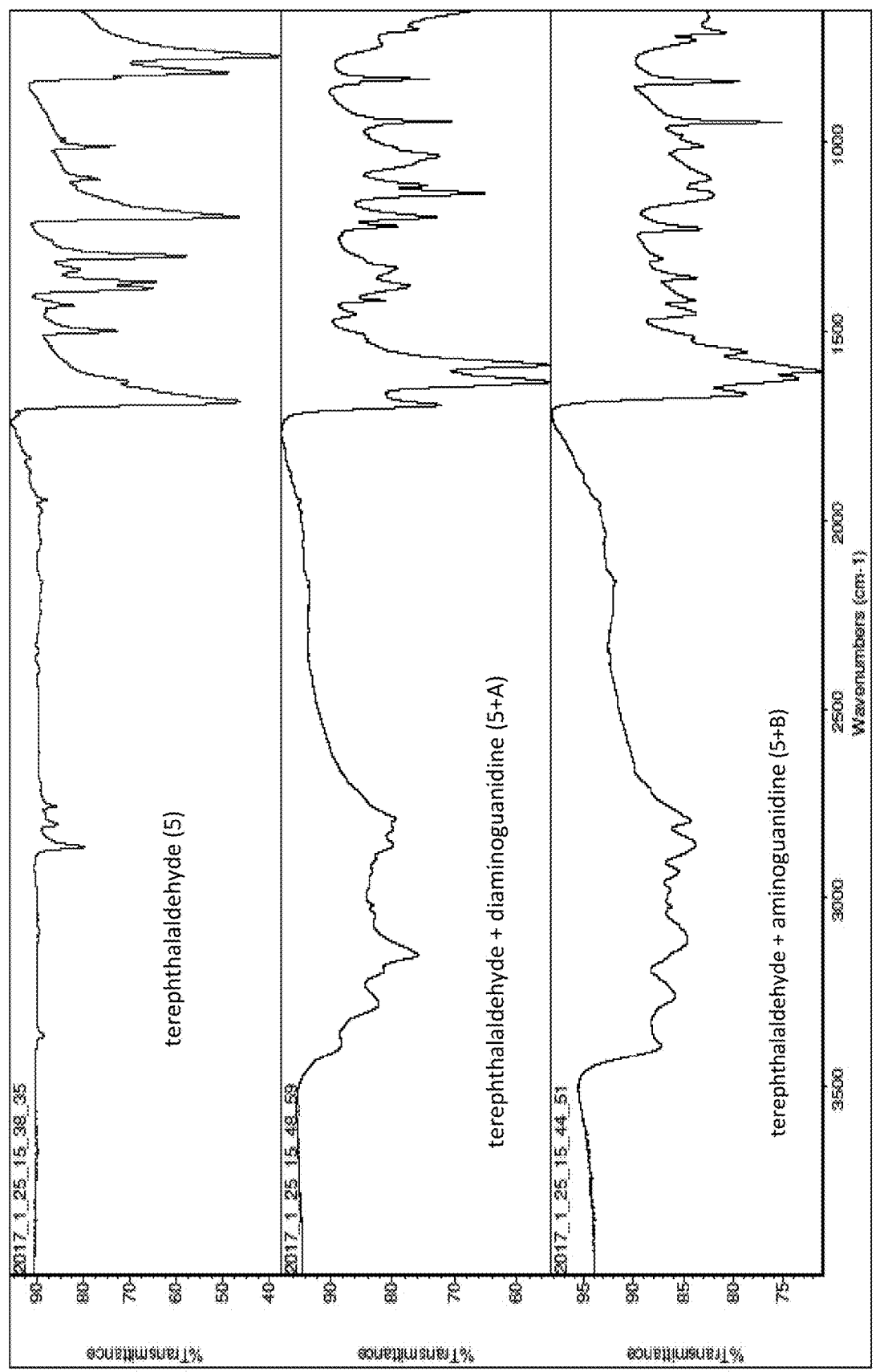
FIG. 3 shows IR spectra of an aldehyde alone and in combination with two different amines, demonstrating the formation of the hydrazone bond, as described below.

The formation of complexes through a hydrazone bond was confirmed through IR spectroscopy. FIG. 3 shows exemplary IR spectrographs for teraphthaldehyde only (top), and teraphthaldehyde combined with aminoguanidine or diaminoguanidine (middle and bottom, respectively). The concomitant disappearance of the aldehyde peak (~1650-1700 $cm^{-1}$) and appearance of the hydrazone peak (~1550-1650 $cm^{-1}$) is clear for both of the middle and bottom spectra.

To compare antimicrobial efficacy of self-assembled complexes to their components, fractional inhibitory concentration indices (FICIs) were calculated from measured minimum inhibitory concentrations (MICs) against *Pseudomonas aeruginosa* and *Escherichia coli*. The MIC of each substance was determined according to standard guidelines in cation-adjusted Mueller-Hinton broth at a total volume of ~100 μl with test concentrations decreasing two-fold to span the empirically-determined MIC (J. Med. Chem., 59: 2126-2138 (2016)). Wells contained starting microbe concentrations of approximately $10^7$ cells/mL. Absorbance at 600 nm (abs600) was determined immediately after inoculation using a 96 well plate reader. Plates were incubated at 37° C. and abs600 measured after 24 hours. For the purposes of these experiments, minimum inhibitory concentrations are defined as the minimum concentration observed to inhibit microbial growth over this time span, with a change in abs600 less than or equal to 0.1.

Following MIC testing, FICI were calculated as shown in Equation 1:

$$FICI_{XY} = \frac{MIC\ X_{combination}}{MIC\ X_{alone}} + \frac{MIC\ Y_{combination}}{MIC\ Y_{alone}} \quad \text{(Equation 1)}$$

The FICI can be used to quantify the synergy between two components (X and Y). Specifically, 1/FICI can be used as a measure of synergy, interpreted as factors by which the potency of a given combination is greater than the sum of its parts (see Journal of Antimicrobial Chemotherapy, 52:1 (2003)). For example, in the present invention, synergy may be found when the effective amount of the self-assembled active agent is lower than the sum of the effective amounts of the two or more component molecules.

Neutral oxygen and sulfur-containing analogues of A and B were treated with aldehydes 1-7. Under otherwise identical conditions, these neutral analogues failed to exhibit significant synergies (1/FICI<5) (data not shown).

Figure 4:
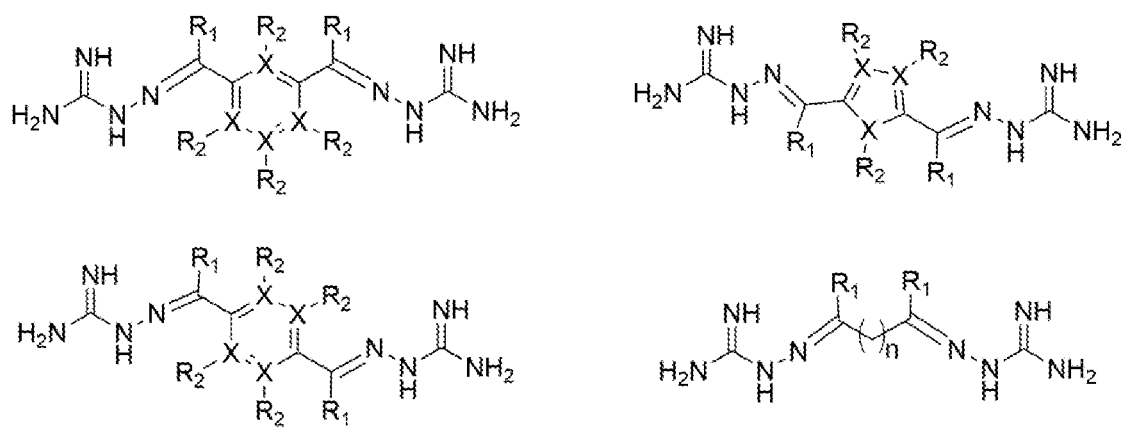
FIG. 4 shows general schema for some of the self-assembled active agents described by the current invention as described below.
Figure 5A:
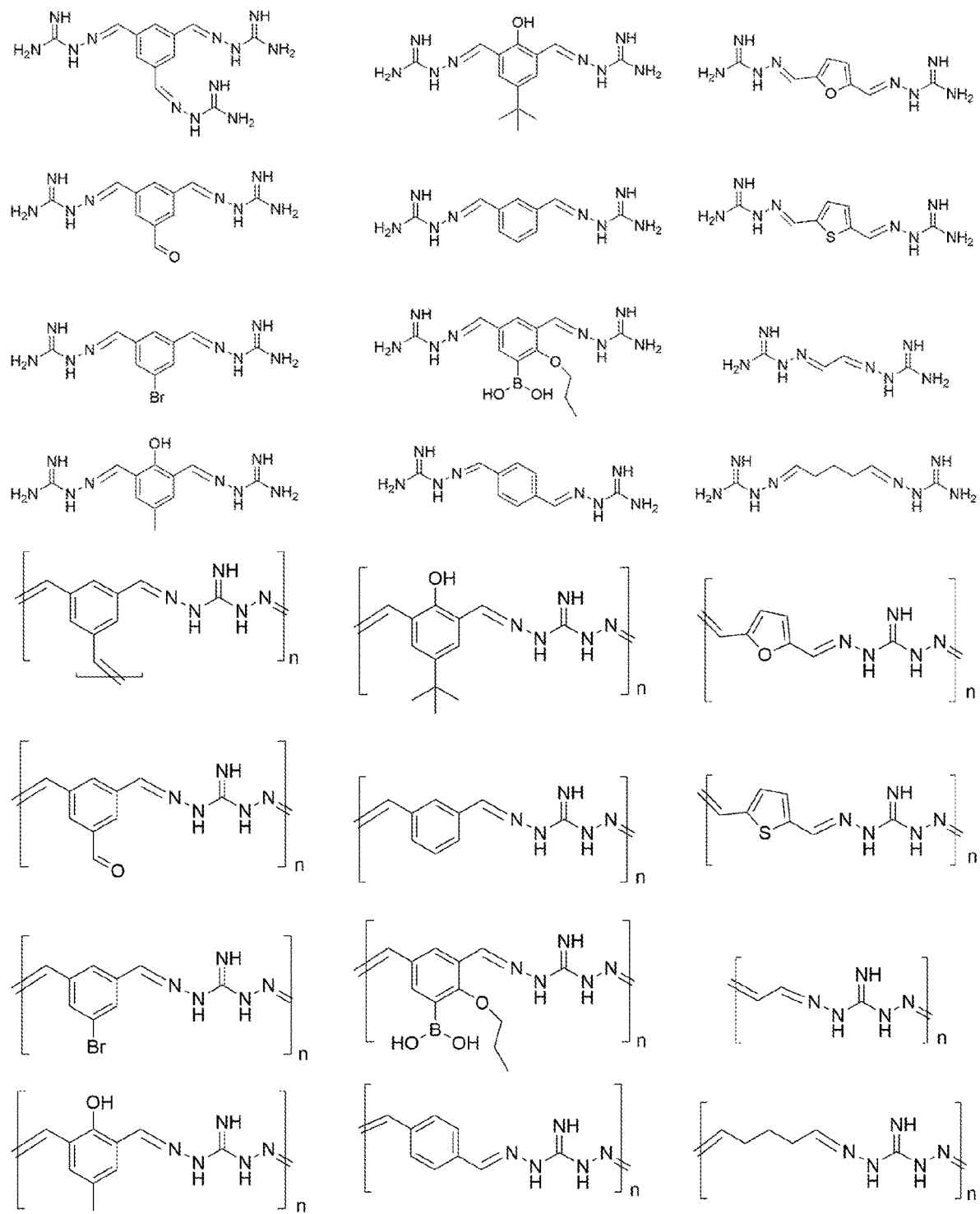
FIG. 5A, FIG. 5B, FIG. 5C and FIG. 5D show structures for some particular self-assembled active agents as described below; a crisscrossed bond indicates that a double bond may be in either the cis or trans configuration.
Figure 5B:
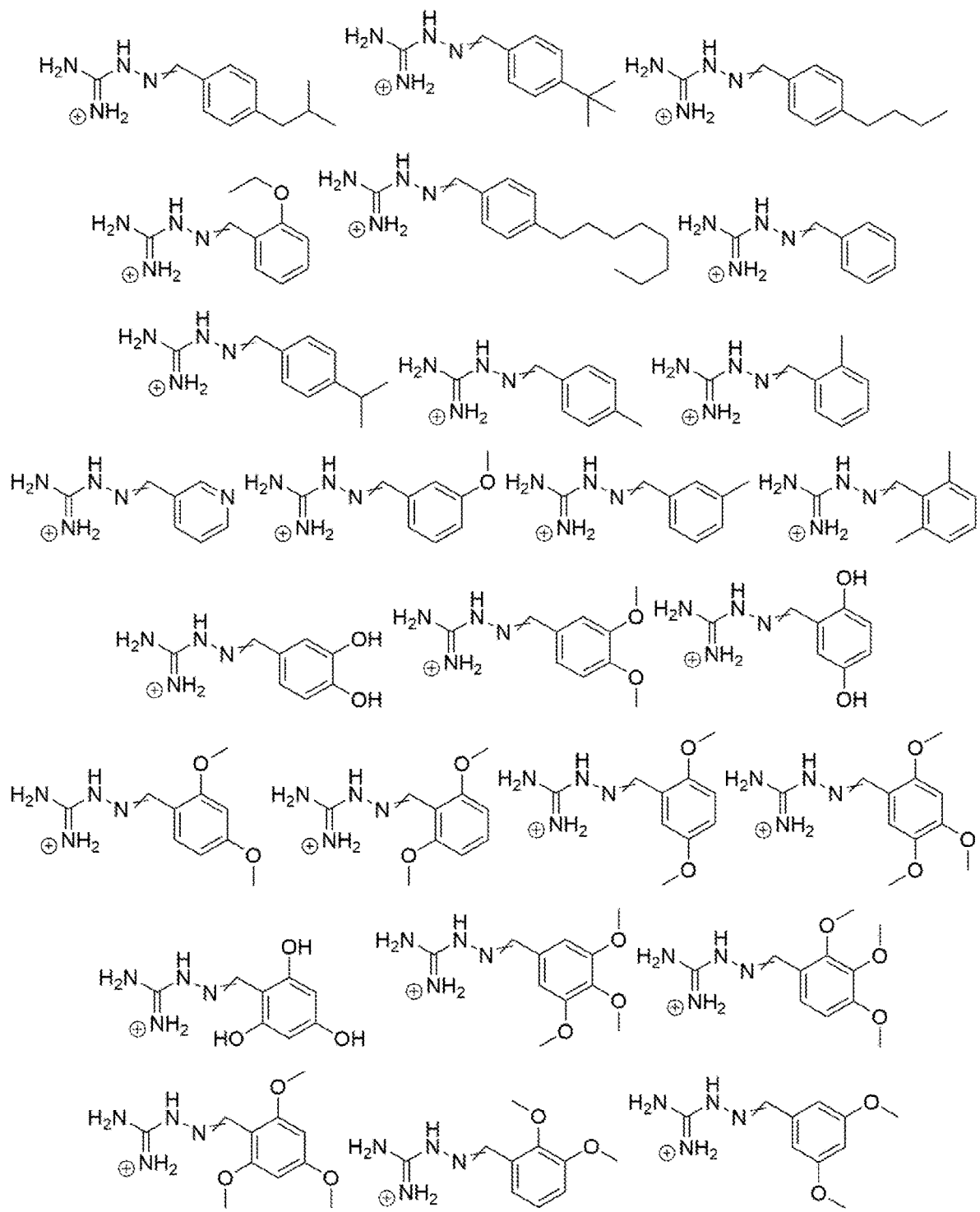
Figure 5C:
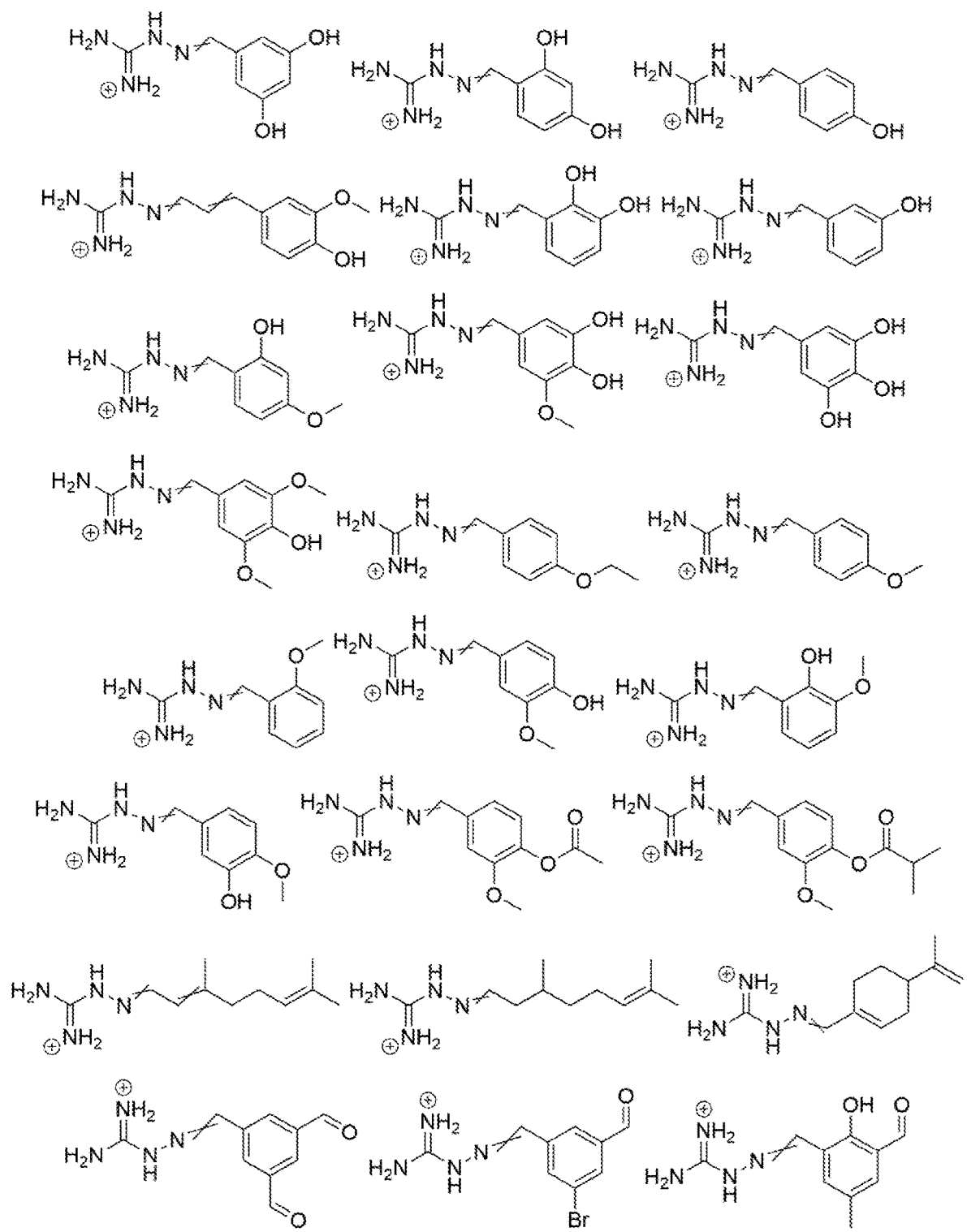
Figure 5D:
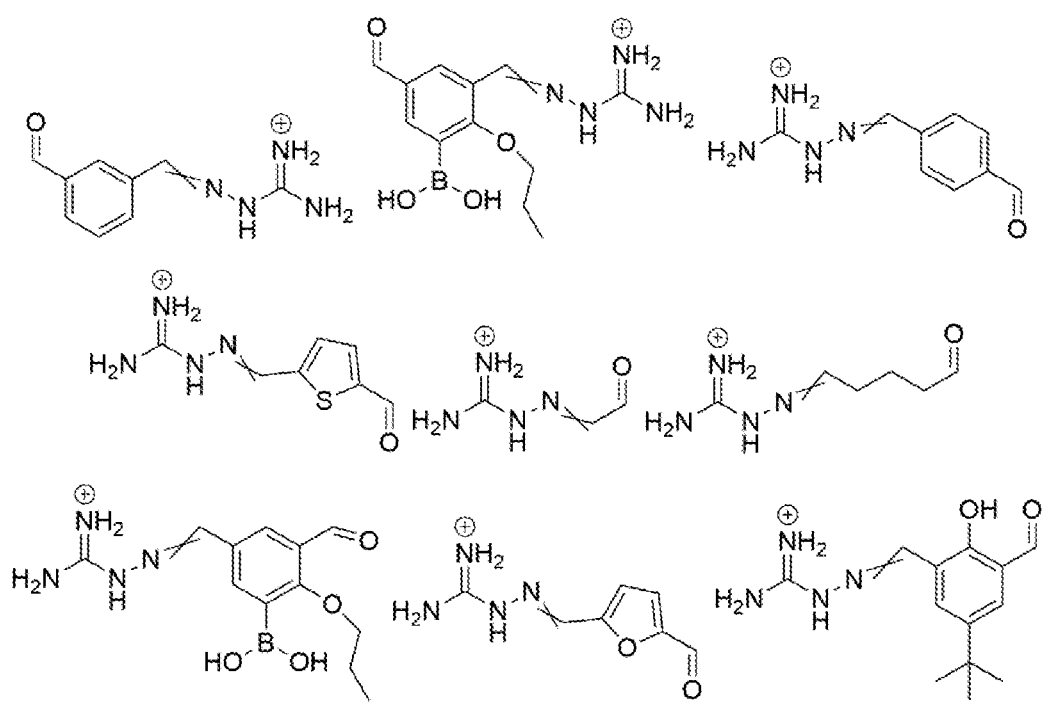

MICs for combinations of A and B with aldehydes 1-13 were measured as against *P. aeruginosa* and *E. coli*. General schema for some of the studied compounds are shown in FIG. 4. Specifically shown in FIG. 4 are general structures showing compound B combined in a complex with any of compounds 6, 8, or 11 (top left), 12 or 13 (top right), 5 (bottom left), and 1 or 2 (bottom right). It is noted that for designations $R_1$, $R_2$, $R_3$, and X, the represented atom(s) need not be the same within the same structure. For example, the top left structure represents B+8 if $R_1$ is H and $R_2$ represents both H and Br. This simplified version is thus used for brevity. The specific structures formed by the combinations of each of A and B with compounds 1, 2, and 4-13 can be found in the list in FIG. 5A, for example.

An exemplary set of measured MICs is shown in Table 2. For the data in Table 2, when multiple components were used to form a complex, the amine component was present in excess of a 1:1 molar ratio.

The MICs determined as per above were then used to calculate FICIs. Synergism (1/FICI) was then tabulated, as shown in Table 3. Note that 1/FICI values varied with subcomponent ratio; unless otherwise noted, the values shown in Table 3 represent a molar ratio of 6:1, amine:aldehyde.

It is noted that of the studied compounds, the aldehydes with the strongest synergies in FIG. 5A, FIG. 5B, FIG. 5C, and FIG. 5D generally are aromatic compounds with two or more aldehyde groups. Further, though B tended to exhibit synergy with compound 5, 6, and 7, glyoxal (1) exhibited greater synergy with A than B by a small but notable margin.

Figure 6:
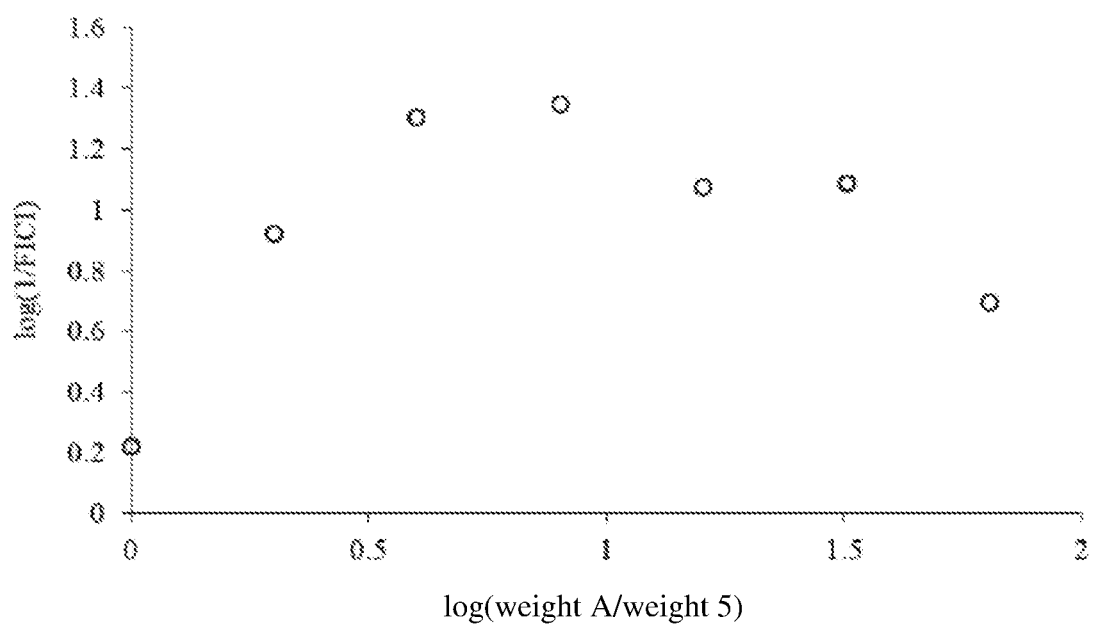
FIG. 6 shows the effect of varying weight ratios of the component compounds on synergy (1/FICI) (FICI=fractional inhibitory concentration indices) for a particular self-assembled active agent as described below.

In addition, relative concentration of components was studied. Components A and 5 were combined in varying ratios to determine a maximum effective FICI. The conditions were that *P. aeruginosa* was grown in Mueller-Hinton broth under aerobic conditions and with a starting concentration of $10^5$ cells/mL. Growth was assessed after 24 hours at 37° C. The weight ratios of A:5 were 1:1, 2:1, 4:1, 8:1, 16:1, 32:1, and 64:1. The results are shown in FIG. 6. As can be seen, the maximum synergy was achieved with the 8:1 weight ratio.

Figure 7:
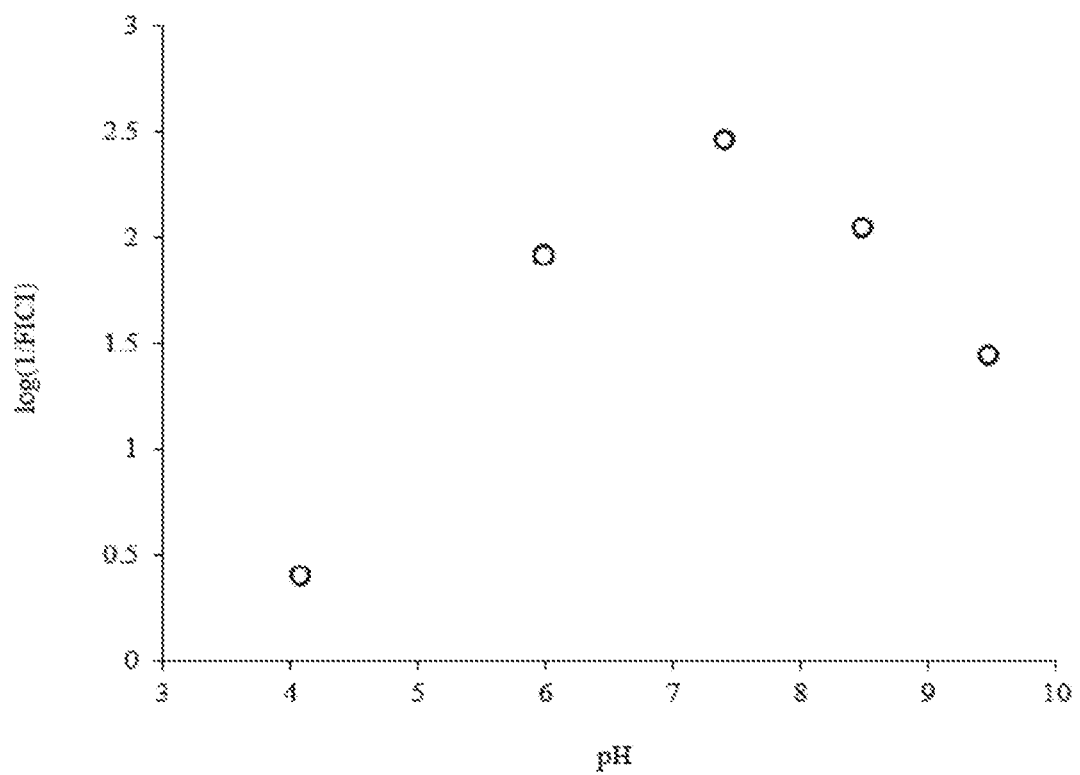
FIG. 7 shows the effect of pH on synergy (1/FICI) for a particular self-assembled active agent as described below.

The effect of pH on synergy was also studied. Components B and 7 were combined in a 3:1 ratio (B:7). *P. aeruginosa* was grown in Mueller-Hinton broth under aerobic conditions and with a starting concentration of $10^5$ cells/mL. Growth was assessed after 24 hours at 37° C. The results are shown in FIG. 7. Synergy decreased markedly as pH diverged from 7.

Other Activities: Activity against the toxin-producing blue-green algae (cyanobacteria) *Microcystis aeruginosa* was also observed in a combination of B+6 (MIC (wt %) Component B: 0.001; Component 6: 0.0001). Thus, the agents also have activity as against photosynthetic organisms (e.g., algae, plants) and/or as an herbicide.

Additional Examples. Formulas: Manual Dish Cleaner (MDC) and All Purpose Cleaner (APC) obtained from UL's Prospector (www.ulprospector.com; accessed 4 PM, 9-15-17): MDC: Water 78.0%, Plantapon 611L UP (Sodium Laureth Sulfate, Lauryl Glucoside, Cocoamidopropyl Betaine, 22.0%); APC: Water 91.68%; Glucopon 420 UP (Caprylyl//Myristyl Glucoside 3.50%, Citric Acid 0.40%, NaOH 0.52%, $NaHCO_3$ 0.40%, Ethanol 3.50%).

General procedure for preparation of actives: Complexes were formed by treating 20 mg of aldehyde or ketone with 180 mg of aminoguanidine HCl stock solution (37 wt % aminoguanidine HCl in $dH_2O$) and heating at 60° C. for 48 h. The resulting product mixtures were subsequently screened for antimicrobial activity.

Minimum inhibitory concentrations (MIC) determination: MIC were determined similarly as previously reported (Design and Testing of Safer, More Effective Preservatives for Consumer Products—ACS Sustainable Chemistry & Engineering (ACS Publications) with one exception: actives were dissolved in an all-purpose cleaner and diluted in Mueller Hinton (MH) broth. A cleaning formulation (generic All Purpose Cleaner or Manual Dish, as mentioned in "Formulas") was used to test compatibility of actives with a representative product formulation.

Viability of microbes in formula over time: The viability of microorganisms were determined by adding complexes in 0.05-1 wt % to formulations (all-purpose cleaner and manual dish) and inoculation with *Aspergillus brasiliensis* (ATCC 16404) to make a total cell concentration of ~$1\times10^6$ spores/mL. The total volume of the mixture was 5 mL. The inoculated mixture was kept in a shaker at 30° C. for 7 days. Microorganism viability was determined by plating 100 am of inoculated mixture on MH agar plates on days 0, 3, and 7.

Results and discussion: Following treatment with aminoguanidine, a library of 54 aldehydes were evaluated as fungal inhibitors (Table 4; conditions: spores/mL, time, temp). The most potent of these complexes were re-evaluated alongside parent aldehydes under similar experimental conditions (Table 5; conditions: spores/mL, time, temp).

Surprisingly aminoguanidine complexes with benzaldehydes were generally more potent than their parent aldehydes. Increases in potency surprisingly ranged from one to two orders of magnitude (Table 5). The most potent of these complexes were added in formula (all-purpose cleaner and manual dish) at 0.1 wt %. A. *Brasiliensis* cell counts were monitored and counted over seven days.

The potency of the aminoguanidine complexes against microbes were affected by the formulation that they were placed in. The manual dish formulation surprisingly inhibited the potency of the aminoguanidine complex against the microbes, as observed by the logarithmic reduction of one (Table 6).

Without being bound by theory, the reversible complexes are hypothesized to disrupt cellular membranes in a manner analogous to quaternary ammonium compounds (quats) and guanide based antimicrobials, such as chlorhexidine and polyhexamethyleneguanidine (Jennings, M. C., et al., ACS Infect. Dis., 1: 288-303 (2015)). In contrast to these conventional antimicrobials, reversible complexes are designed to dissociate to nontoxic, biodegradable subcomponents after use. This process is anticipated to minimize collateral toxicity and antimicrobial resistance.

Producers are facing growing restrictions on use of biocides with poor human and environmental Producers health attributes. Reversible antimicrobials, such as those described herein, may compete with current products where consumer and environmental safety is a prominent concern. In cases where current biocides are being heavily regulated, reversible analogues could completely substitute for these products by offering the novel advantage of controlled or predictable dissociation.

Antibiotic resistant infections kill approximately 700,000 people per year. If resistance trends continue, global annual GDP could be reduced by 2-3.5% by 2050, a loss of $60-$100 trillion of cumulative economic output. The persistence of antibiotics that linger in the environment long after their targeted use is a major cause of this problem. Antibiotics currently used for agriculture may be replaceable by inexpensive, biobased, and non-toxic reversible antimicrobials described herein.

Table 7 surprisingly shows good to excellent performance of aminoguanidine-cuminaldehyde complex in home cleaning formulations. This complex was deactivated by high levels of ionic surfactants, such as in the manual dish formulation. Aminoguanidine adducts of more hydrophilic aldehydes (i.e., 4-hydroxybenzaldehyde, 2,6-dimethoxybenzaldehyde, 2,4,6-trimethoxybenzaldehyde, m-anisaldehyde) circumvented deactivation in this manner and enabled effective preservation of the high surfactant manual dish formula.

Tables 8 and 9 show that the addition of aminoguanidine surprisingly increased the antimicrobial properties of complex mixtures of flavors, fragrances and bulk plant extracts and oils that are often rich sources of bioactive aldehydes. Increases in potency were typically one to two orders of magnitude. So the second component can be plant extracts, oils, flavors or fragrances.

Conclusions: Treatment of aldehydes and ketones with aminoguanidine or diaminoguanidine surprisingly affords complexes that exhibit antimicrobial potencies that may be orders of magnitude greater than the sum of their parts. Because complex formation is surprisingly reversible, products dissociate due to thermodynamic changes such as dilution or pH. This property appears to be general to a broad class of substrate aldehydes and ketones, surprisingly enabling the activation of nontoxic subcomponents. As in several of the aforementioned cases (e.g., cuminaldehyde, benzaldehyde, syringaldehyde, vanillin) these subcomponents may be agriculturally-derived, nontoxic and biodegradable. Compared to covalent analogues (e.g., chlorhexidine, polyhexamethyleneguanidine, quaternary ammonium compounds), this class of reversible compounds will minimize the potential for collateral toxicity and antimicrobial resistance by dissociating to nontoxic subcomponents in the environment.

The invention illustratively disclosed herein suitably may be practiced in the absence of any element (e.g., method (or process) steps or composition components) which is not specifically disclosed herein. Thus the specification includes disclosure by silence ("Negative Limitations In Patent Claims," AIPLA Quarterly Journal, Tom Brody, 41(1): 46-47 (2013):

" . . . Written support for a negative limitation may also be argued through the absence of the excluded element in the specification, known as disclosure by silence . . . .

Silence in the specification may be used to establish written description support for a negative limitation. As an example, in Ex parte Lin [No. 2009-0486, at 2, 6 (B.P.A.I. May 7, 2009)] the negative limitation was added by amendment . . . In other words, the inventor argued an example that passively complied with the requirements of the negative limitation . . . was sufficient to provide support . . . .

This case shows that written description support for a negative limitation can be found by one or more disclosures of an embodiment that obeys what is required by the negative limitation . . . ."

The foregoing description and accompanying figures illustrate the principles, preferred embodiments, and modes of operation of the invention. However, the invention should not be construed as being limited to the particular embodiments discussed above. Additional variations of the embodiments discussed above will be appreciated by those skilled in the art.

Therefore, the above-described embodiments should be regarded as illustrative rather than restrictive. Accordingly, it should be appreciated that variations to those embodiments can be made by those skilled in the art without departing from the scope of the invention as defined by the following claims.

The composition when it contains only one active compound does not contain the following compounds:

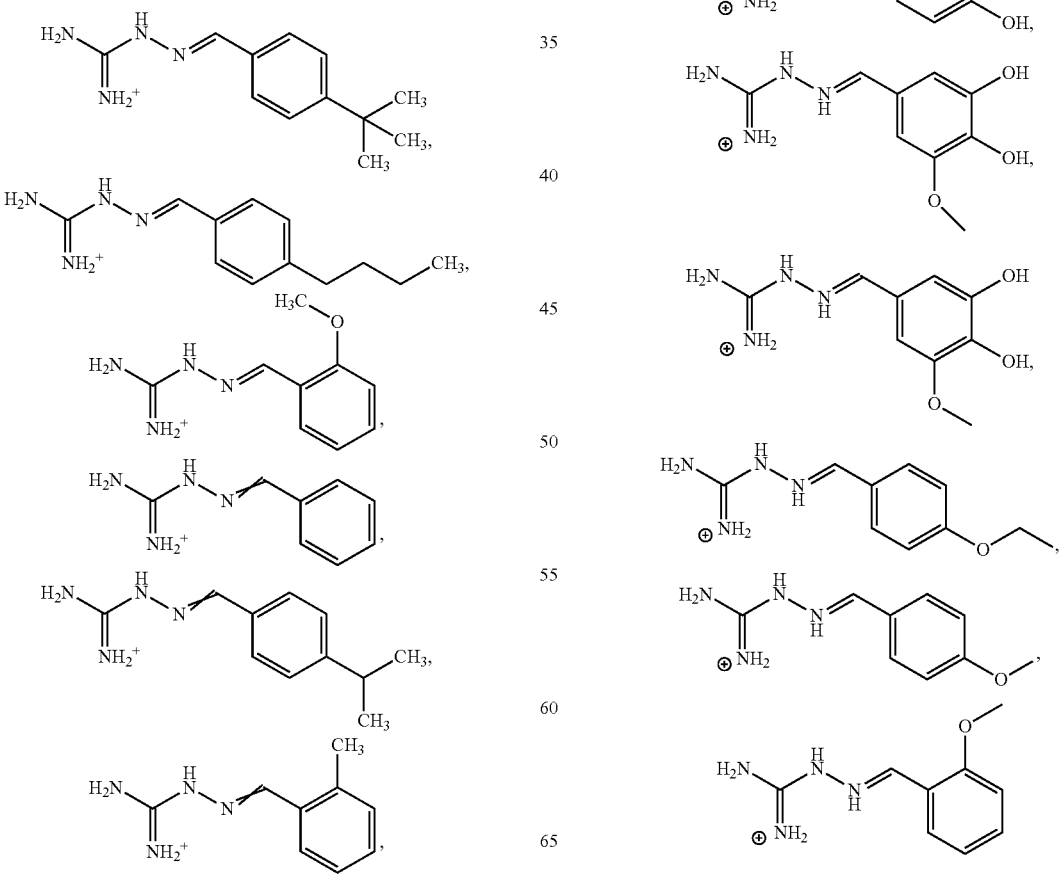

-continued

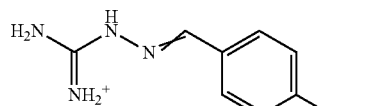

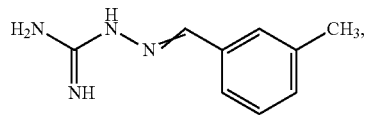

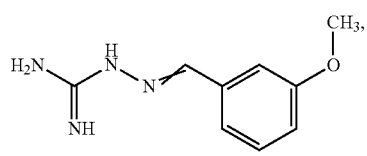

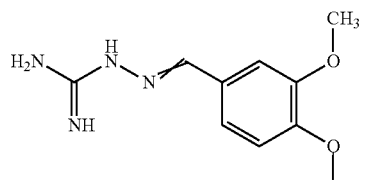

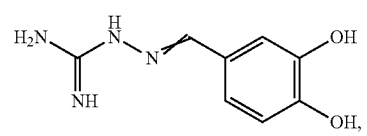

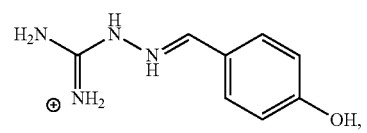

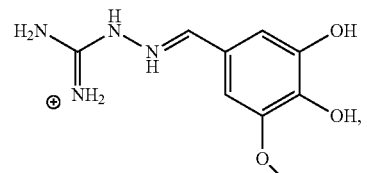

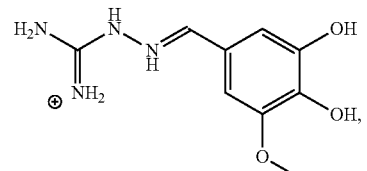

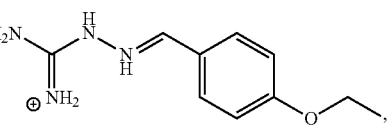

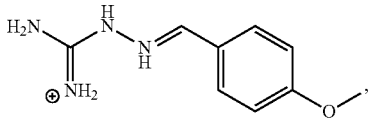

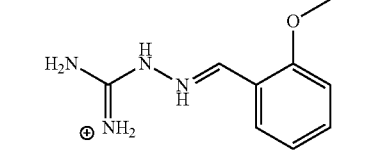

-continued

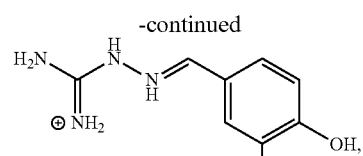

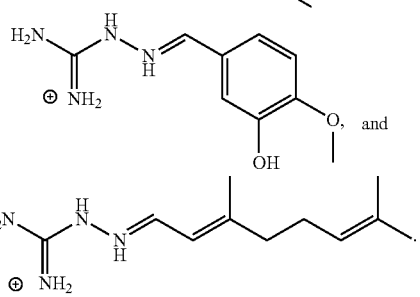

This trypanocidal compound is not used by itself as a trypanocidal compound:

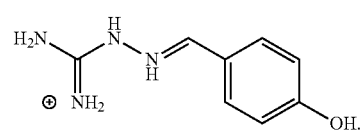 [SMILES: N=C(N)N/N=C/c1ccc(O)cc1]

This anti-malarial compound is not used by itself as an anti-malarial compound:

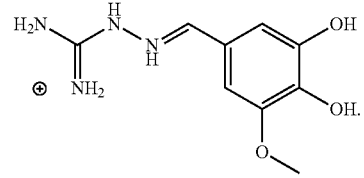 [SMILES: COc1cc(/C=N/NC(=N)N)cc(O)c1O]

This anti-protozoa and anti-bacterial compound is not used by itself as an anti-protozoa and anti-bacterial compound:

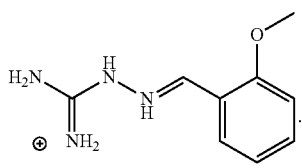

This anti-fungal compound is not used by itself as an anti-fungal compound:

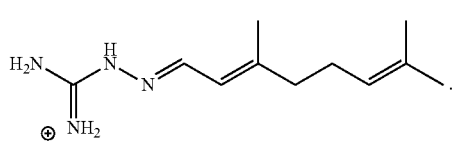

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

| | Exemplary Components | |
|---|---|---|
| | Compound Name (designation) | Compound Structure |
| Amines | 1,3-diamino-guanidine (A) | |
| | aminoguanidine (B) | |
| Aldehydes | glyoxal (1) | |
| | glutaraldehyde (2) | |
| | benzylaldehyde (3) | |
| | phthalaldehyde (4) | |
| | terephthalaldehyde (5) | |
| | isophthalaldehyde (6) | |
| | benzene-1,3,5-tricarboxaldehyde (7) | |
| | 2-Bromoiso-phthalaldehyde (8) | |
| | 4-tBu-2,6-diformylphenol (9) | |

TABLE 1-continued

Exemplary Components

| Compound Name (designation) | Compound Structure |
|---|---|
| 4-Me-2,6-diformylphenol (10) | 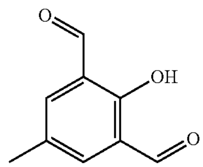 |
| 3,5-Diformyl-2-propoxyphenylboronic acid (11) | 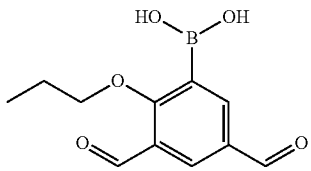 [SMILES: CCCOc1c(C=O)cc(C=O)cc1B(O)O] |
| 2,5-thiophene-dialdehyde (12) | 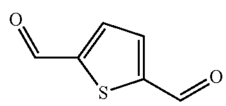 |
| 2,5-furandialdehyde (13) | 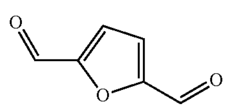 |

TABLE 2

MICs for Lone Components and Complexes

| Conditions | Component | MIC (wt %) |
|---|---|---|
| alone | A | $0.3^{i}$ |
|  | B | $>2^{i}$ |
|  | 1 | $0.04^{i}$ |
|  | 5 | $0.3^{i}$ |
|  | 7 | $0.3^{i}$ |
| A + 1 | A | $0.008^{i}$ |
|  | 1 | $0.001^{i}$ |
| A + 5 | A | $0.006^{i}$ |
|  | 5 | $0.001^{i}$ |
| A + 7 | A | $0.002^{i}$ |
|  | 7 | $0.003^{i}$ |
| B + 1 | B | $4^{i}$ |
|  | 1 | $0.7^{i}$ |
| B + 5 | B | $0.06^{i}$ |
|  | 5 | $0.01^{i}$ |
| B + 7 | B | $0.002^{i}$ |
|  | 7 | $0.0003^{i}$ |
| B + 8 | B | $0.004^{ii}$ |
|  | 8 | $0.0004^{ii}$ |
| B + 9 | B | $0.00005^{ii}$ |
|  | 9 | $0.00001^{ii}$ |
| B + 10 | B | $0.02^{ii}$ |
|  | 10 | $0.002^{ii}$ |
| B + 11 | B | $0.03^{ii}$ |
|  | 11 | $0.003^{ii}$ |
| B + 12 | B | $0.007^{ii}$ |
|  | 12 | $0.001^{ii}$ |
| B + 13 | B | $0.01^{ii}$ |
|  | 13 | $0.005^{ii}$ |

$^{i}$P. aeruginosa;
$^{ii}$E. coli

TABLE 3

Synergism (1/FICI) of Several Aldehydes and Amines

| Component | A | B |
|---|---|---|
| 1 | 20 | 0.1 |
| 2 | 3 | <5 |
| 3 | <5 | <5 |
| 4 | 3 | <5 |
| 5 | 20 | 20 |
| 6 | 30 | 200 |
| 7 | 20 | 1000* |

*extrapolated from eight FICI measurements where the weight ratio of B:7 varied from 1:1 to 9:1.

TABLE 4

Minimum inhibitory concentrations (MICs) of aminoguanidine-aldehyde adducts against A. brasiliensis ATCC16404. (4 × $10^5$ spores/mL starting spore counts)

| Entry | ALDEHYDE (R1, R2 = H for all) | MIC (wt %) |
|---|---|---|
| 1 | 4-isobutylbenzaldehyde | 0.0074 |
| 2 | 4-tert-butylbenzaldehyde | 0.0298 |
| 3 | 4-butylbenzaldehyde | 0.1190 |
| 4 | 4-octylbenzaldehyde | 0.0149 |
| 5 | 2-ethoxybenzaldehyde | 0.0149 |
| 6 | benzaldehyde, redistilled | 0.1190 |
| 7 | cuminaldehyde, stock | 0.0074 |
| 8 | o-tolualdehyde | 0.0595 |
| 9 | p-tolualdehyde | 0.1190 |
| 10 | 3-pyridinecarboxaldehyde | 0.1190 |
| 11 | m-tolualdehyde | 0.1190 |
| 12 | m-anisaldehyde | 0.0595 |
| 13 | cuminaldehyde, from oil | 0.0149 |
| 14 | cuminaldehyde, from bath | 0.0298 |
| 15 | veratraldehyde | 0.0149 |
| 16 | 2,6-dimethylbenzaldehyde | 0.0298 |
| 17 | 2-bromoisophthalaldehyde | 0.0074 |
| 18 | 2-hydroxy-5-methyl-1,3-benzenedicarboxaldehyde | 0.0149 |
| 19 | 2,5-thiophenedicarboxaldehyde | 0.0149 |
| 20 | 2,5-furandicarboxaldehyde | 0.0074 |
| 21 | 3,4-dihydroxybenzaldehyde | 0.0595 |
| 22 | 2,6-dimethoxybenzaldehyde | 0.0149 |
| 23 | 2,5-dimethoxybenzaldehyde | 0.0149 |
| 24 | 2,4-dimethoxybenzaldehyde | 0.0149 |
| 25 | 2,4,6-trihydroxybenzaldehyde | 0.0298 |
| 26 | 3,4,5-trimethoxybenzaldehyde | 0.4762 |
| 27 | 2,4,5-trimethoxybenzaldehyde | 0.4762 |
| 28 | 2,3,4-trimethoxybenzaldehyde | 0.1190 |
| 29 | 2,4,6-trimethoxybenzaldehyde | 0.0595 |
| 30 | 2,3-dimethoxybenzaldehyde | 0.0298 |
| 31 | 3,5-dimethoxybenzaldehyde | 0.0595 |
| 32 | 3,5-dihydroxybenzaldehyde | 0.1190 |
| 33 | 2,5-dihydroxybenzaldehyde | 0.1190 |
| 34 | 2,4-dihydroxybenzaldehyde | 0.2381 |
| 35 | 4-hydroxybenzaldehyde | 0.0298 |
| 36 | 4,6-dimethoxysalicylaldehyde | 0.0298 |
| 37 | 2,3-dihydroxybenzaldehyde | 0.0149 |
| 38 | 3-hydroxybenzaldehyde | 0.0149 |
| 39 | 4-hydroxyl-3-methoxycinnamaldehyde see entry 34 | 0.0298 |
| 40 | 2-hydroxyl-4-methoxybenzaldehyde | 0.0149 |
| 41 | 3,4-dihydroxy-5-methoxybenzaldehyde | 0.0595 |
| 42 | 3,4-dihydroxy-5-hydroxybenzaldehyde | 0.0298 |
| 43 | Syringaldehyde | 0.0149 |
| 44 | 4-ethoxybenzaldehyde | 0.0595 |
| 45 | 2,6-dimethoxy-4-hydroxybenzaldehyde | 0.2381 |
| 46 | 1,3,5-triformylbenzene | 0.4762 |
| 47 | p-anisaldehyde | 0.1190 |
| 48 | o-anisaldehyde | 0.0298 |
| 49 | vanillin | 0.4762 |
| 50 | o-vanillin | 0.0595 |
| 51 | isovanillin | 0.0595 |

TABLE 4-continued

Minimum inhibitory concentrations (MICs) of aminoguanidine-aldehyde adducts against *A. brasiliensis* ATCC16404. (4 × $10^5$ spores/mL starting spore counts)

| Entry | ALDEHYDE (R1, R2 = H for all) | MIC (wt %) |
|---|---|---|
| 52 | vanillin acetate | 0.2381 |
| 53 | vanillin isobutyrate | 0.1190 |

TABLE 5

Minimum inhibitory concentrations of aminoguanidine complexes compared to subcomponents (aldehyde, aminoguanidine or biocide standard Kathon CG) against *A. brasiliensis* ATCC 16404.

| Entry | ALDEHYDE (R1, R2 = H for all) | MIC (wt %) Complex | MIC (wt %) subcomponent |
|---|---|---|---|
| 1 | 4-isobutylbenzaldehyde | 0.0595 | 0.4762 |
| 4 | 4-octylbenzaldehyde | 0.0595 | 0.4762 |
| 5 | 2-ethoxybenzaldehyde | 0.0595 | 0.4762 |
| 7 | cuminaldehyde, stock | <0.0037 | 0.4752 |
| 15 | veratraldehyde | 0.0595 | 0.4762 |
| 17 | 2-bromoisophthalaldehyde | <0.0037 | 0.0595 |
| 18 | 2,5-dihydroxybenzaldehyde | >0.4762 | >0.4762 |
| 19 | 2-hydroxy-5-methyl-1,3-benzenedicarboxaldehyde | <0.0037 | 0.0595 |
| 20 | 2,5-thiophenedicarboxaldehyde | <0.0037 | 0.0595 |
| 21 | 2,5-furandicarboxaldehyde | 0.0149 | 0.1190 |
| 24 | 2,5-dimethoxybenzaldehyde | 0.1190 | 0.2381 |
| 25 | 2,4-dimethoxybenzaldehyde | 0.0298 | 0.4762 |
| 38 | 2,3-dihydroxybenzaldehyde | >0.4762 | >0.4762 |
| 39 | 3-hydroxybenzaldehyde | >0.4762 | 0.1190 |
| 41 | 2-hydroxyl-4-methoxybenzaldehyde | 0.0298 | 0.2381 |
| 44 | syringaldehyde | 0.1190 | >0.4762 |
| — | Amino Guanidine | — | >0.4762 |
| — | Kathon cg | — | 0.0149 |

TABLE 6

Viability of microorganisms over seven days, measured by the logarithmic reduction in cell count of *A. Brasiliensis* (initial concentration = $5 \times 10^6$ cells/mL).

| Entry | ALDEHYDE (R1, R2 = H for all) | Log Reduction in APC formula | Log Reduction in MDC formula |
|---|---|---|---|
| 7 | cuminaldehyde, stock | 5 | 1 |
| 17 | 2-bromoisophthalaldehyde | 2 | 1 |
| 19 | 2-hydroxy-5-methyl-1,3-benzenedicarboxaldehyde | 4 | 1 |
| 20 | 2,5-thiophenedicarboxaldehyde | 2 | 1 |
| 21 | 2,5-furandicarboxaldehyde | 1 | 1 |
| 25 | 2,4-dimethoxybenzaldehyde | 6 | 1 |
| 41 | 2-hydroxyl-4-methoxybenzaldehyde | 1 | 1 |
| — | Kathon cg | 6 | 6 |

TABLE 7

Preservative Test Results of Reversible Antimicrobial in Home Cleaning Formulations

| Formula | Antimicrobial | Concentration (wt. %) | Log reduction in formula: *Aspergillus brasillensis*, ATCC16404 | Log reduction in formula: *Pseudomonas aeruginosa* ATCC9027 |
|---|---|---|---|---|
| Shower Spray | Aminoguanidine + cuminaldehyde | 1 | Fail* | Pass |
| Shower Spray | Aminoguanidine + cuminaldehyde | 0.2 | Fail* | Pass |
| Window Cleaner | Aminoguanidine + cuminaldehyde | 0.2 | Pass | Pass |
| All Purpose Cleaner | Aminoguanidine + cuminaldehyde | 0.1 | Pass | Pass |
| Toilet Cleaner | Aminoguanidine + cuminaldehyde | 0.2 | Pass | Pass |
| Bath Cleaner | Aminoguanidine + cuminaldehyde | 0.2 | Fail* | Pass |
| Hand soap | Aminoguanidine + cuminaldehyde | 0.2 | Pass | Pass |
| Hand lotion | Aminoguanidine + cuminaldehyde | 0.5 | Pass | Pass |
| Manual Dish | Aminoguanidine + cuminaldehyde | 1 | Fail** | Fail** |
| Manual Dish | Aminoguanidine + 4-hydroxybenzaldehyde | 1 | Pass | ND |
| Manual Dish | Aminoguanidine + 2,4,6-trimethydroxybenzaldehyde | 1 | Pass | ND |
| Manual Dish | Aminoguanidine + m-anisaldehyde | 1 | Pass | ND |
| Manual Dish | Aminoguanidine + 2,6-dimethydroxybenzaldehyde | 1 | Pass | ND |
| Key | | 6 log (<1 wk) | 3 log (<1 wk) fail* | <3 log (2 wk) fail** |

TABLE 8

Aminoguanidine may enhance the antimicrobial properties of plant extracts and oils (*E. coli* ATCC 8739)

| | Extract or oil | MIC after aminoguanidine addition (wt %) | MIC Essential Oil (wt %) | Factor increase in potency |
|---|---|---|---|---|
| 1 | Bergamont | 1.25 | greater than 2.5 | 2 |
| 2 | Grapefruit | 2.5 | greater than 2.5 | 1 |
| 3 | Orange | greater than 2.5 | greater than 2.5 | 1 |
| 4 | Spearmint | 1.25 | greater than 2.5 | 2 |
| 5 | Cinnamon | 0.0390625 | 0.15625 | 4 |
| 6 | Lavender | 2.5 | greater than 2.5 | 1 |
| 7 | Patchouli | greater than 2.5 | greater than 2.5 | 1 |
| 8 | Tea Tree Oil | 2.5 | 1.25 | 0.5 |
| 9 | Clary Sage | 2.5 | greater than 2.5 | 1 |
| 10 | Lemongrass | 0.15625 | 2.5 | 16 |
| 11 | Lemon | 1.25 | greater than 2.5 | 2 |
| 12 | Peppermint | 2.5 | greater than 2.5 | 1 |
| 13 | Eucalyptus | greater than 2.5 | greater than 2.5 | 1 |
| 14 | Lime | 2.5 | greater than 2.5 | 1 |
| 15 | Rosemary | 2.5 | 2.5 | 1 |
| 16 | Vanilla | 1.25 | 2.5 | 2 |
| 17 | Vetiver | 1.25 | greater than 2.5 | 2 |
| 18 | Bay Leaf | 2.5 | 2.5 | 1 |
| 19 | Cinnamon cassia | 0.0390625 | 0.078125 | 2 |
| 20 | Tonka Bean | 2.5 | 1.25 | 0.5 |
| 21 | Cedarwood | greater than 2.5 | greater than 2.5 | 1 |
| 22 | Sandalwood | 1.25 | greater than 2.5 | 2 |
| 23 | Clove | 2.5 | 1.25 | 0.5 |
| 24 | Oregano | 0.3125 | 0.15625 | 0.5 |

TABLE 9

Aminoguanidine may enhance the antimicrobial properties of flavors/fragrances (*E. coli* ATCC 8739)

| | Fragrance | MIC after aminoguanidine addition (wt %) | MIC Fragrance (wt %) | Factor increase in potency |
|---|---|---|---|---|
| 1 | Olive Leaf | 0.625 | greater than 2.5 | 4 |
| 2 | Lime and Sea | 0.625 | greater than 2.5 | 4 |
| 3 | Lemon Mint | 0.0390625 | 1.25 | 32 |
| 4 | Eucalyptus Mint (tub/tile) | 0.625 | 2.5 | 4 |
| 5 | Eucalyptus Mint | 0.3125 | 2.5 | 8 |
| 6 | Clementine (Dish) | 0.3125 | greater than 2.5 | 8 |
| 7 | Pink Grapefruit | 0.3125 | greater than 2.5 | 8 |
| 8 | Wisteria | 0.0390625 | 2.5 | 64 |
| 9 | Fresh Lavender | 2.5 | 2.5 | 1 |
| 10 | Lavender Cedar | 0.625 | 2.5 | 4 |
| 11 | Fresh Air | 0.625 | greater than 2.5 | 4 |
| 12 | Waterfall | 0.15625 | greater than 2.5 | 16 |
| 13 | Toasted Vanilla | 1.25 | 2.5 | 2 |
| 14 | Mandarin Mango | 1.25 | greater than 2.5 | 2 |
| 15 | Ginger Mango 4x | 0.625 | 2.5 | 4 |
| 16 | Beach Sage 4x | 2.5 | greater than 2.5 | 1 |
| 17 | Parsley and Thyme | 0.625 | 2.5 | 4 |
| 18 | Mint | 1.25 | 2.5 | 2 |
| 19 | Almond | 0.15625 | 2.5 | 16 |
| 20 | Almond WF | 0.078125 | 2.5 | 32 |

We claim:

1. A composition comprising a compound of the formula:

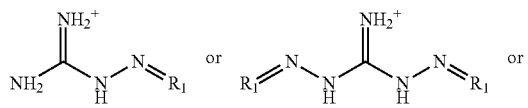

or

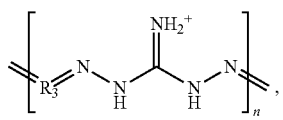

wherein $R_1$ and $R_3$ are, independently, optionally substituted one or more times, wherein in the case of either of $R_1$ or $R_3$ having at least one substitution, a first substitution is one of an alcohol group, an aldehyde group, a 5-member ring, a 6-member ring, a halide, a halide-diol, an ether, and a straight or branched, saturated or unsaturated aliphatic group, wherein n is at least 2, and wherein $R_1$ is one of the following:

 (2)

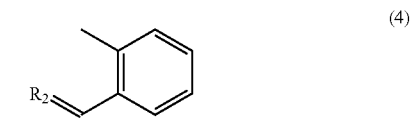 (4)

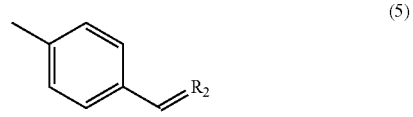 (5)

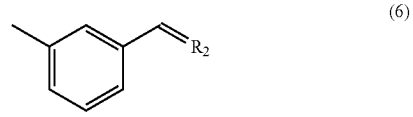 (6)

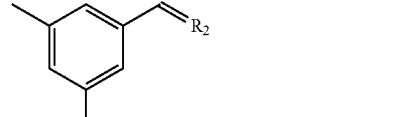 (7)

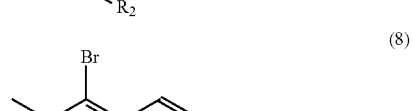 (8)

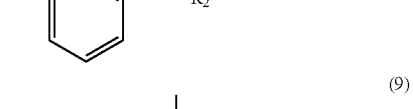 (9)

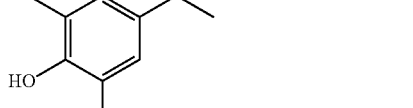 (10)

-continued
(11a) 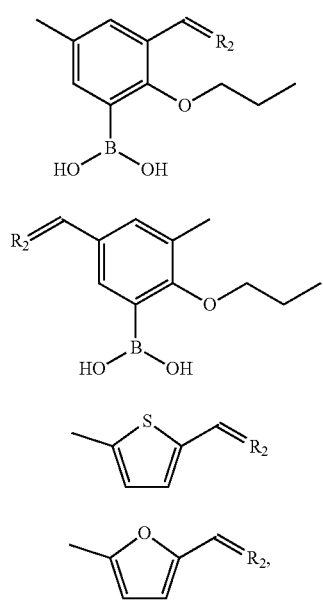
(11b)
(12)
(13)
wherein R₂ is:
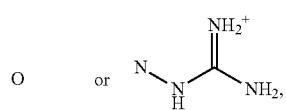
and wherein R₃ is one of:
C₂H₄
C₅H₁₀
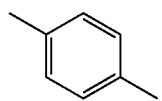
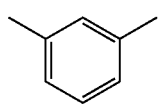
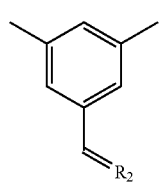
-continued
(G) 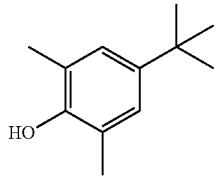
(H) 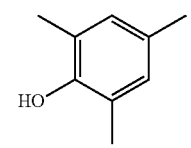
(I) 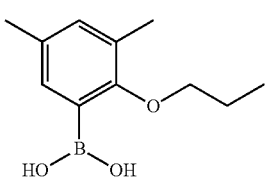
(J) 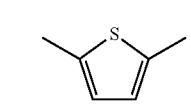
(K) 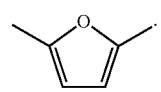
2. A composition comprising a compound, wherein the compound is one of:
(A) 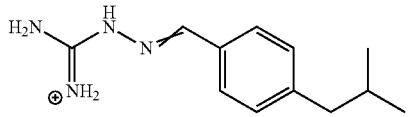
(B) 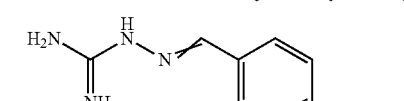
(C) 
(D) 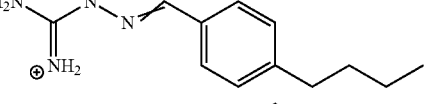
(E) 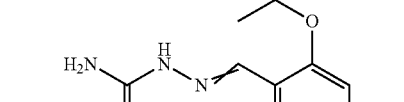
(F) 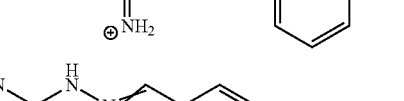
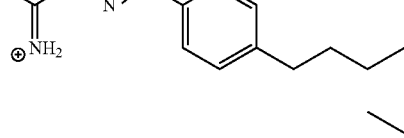

-continued
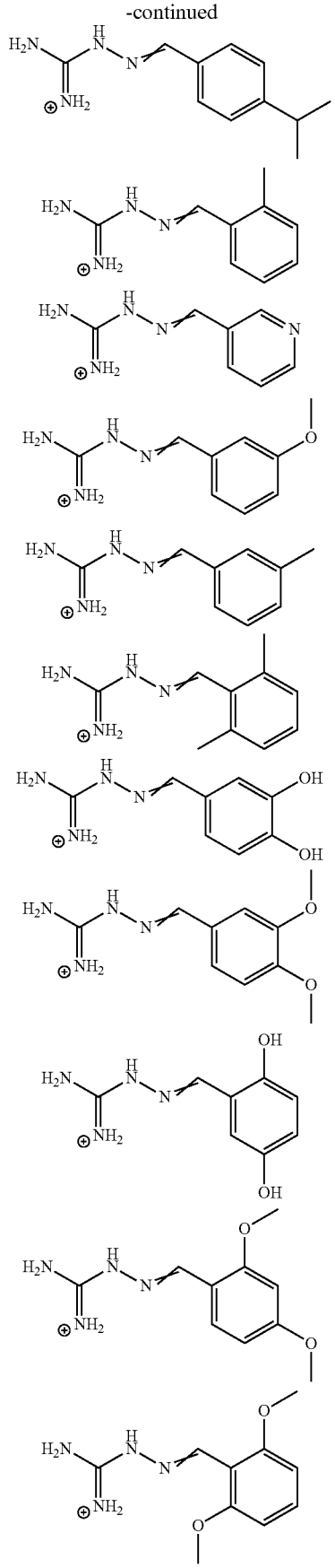
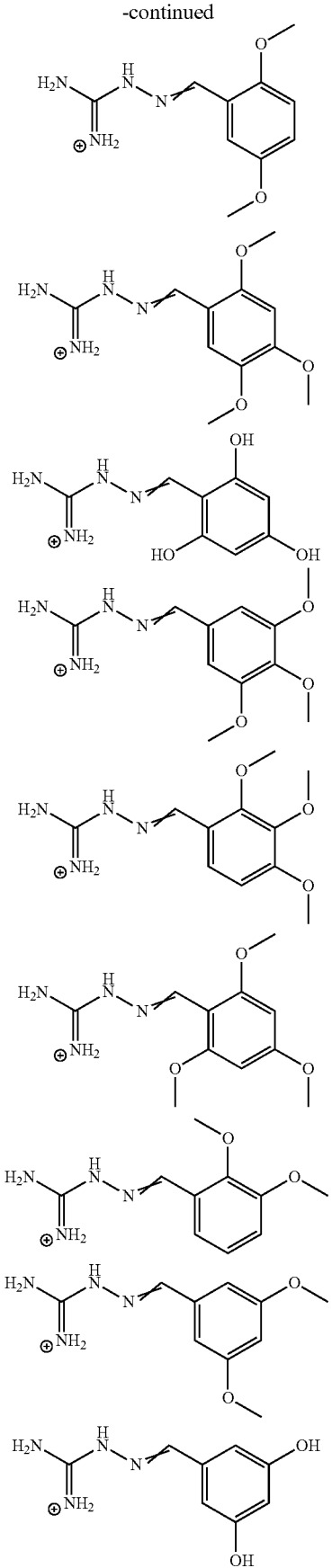

29
-continued
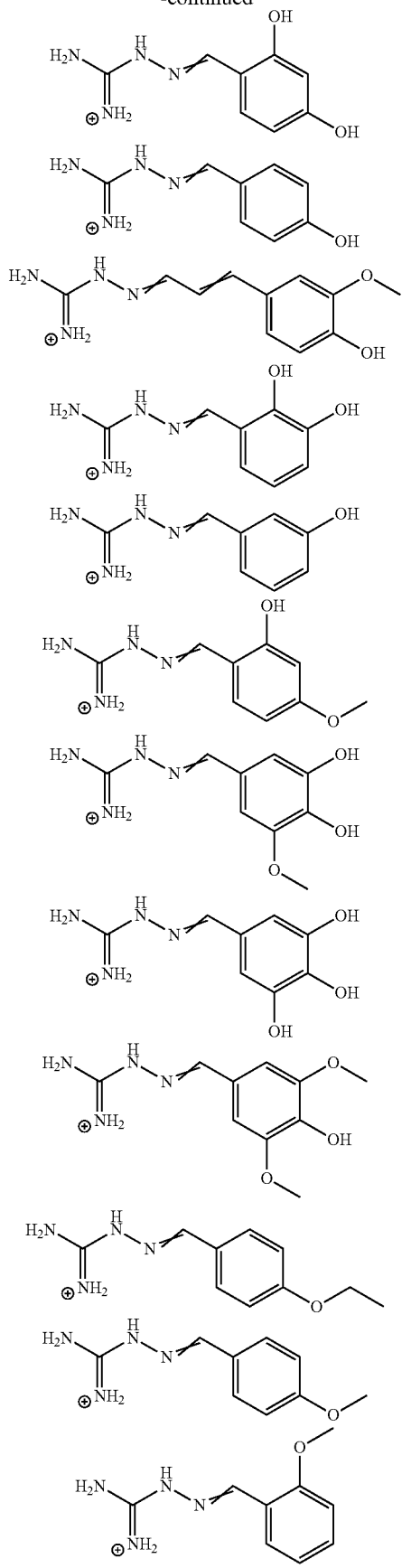
30
-continued
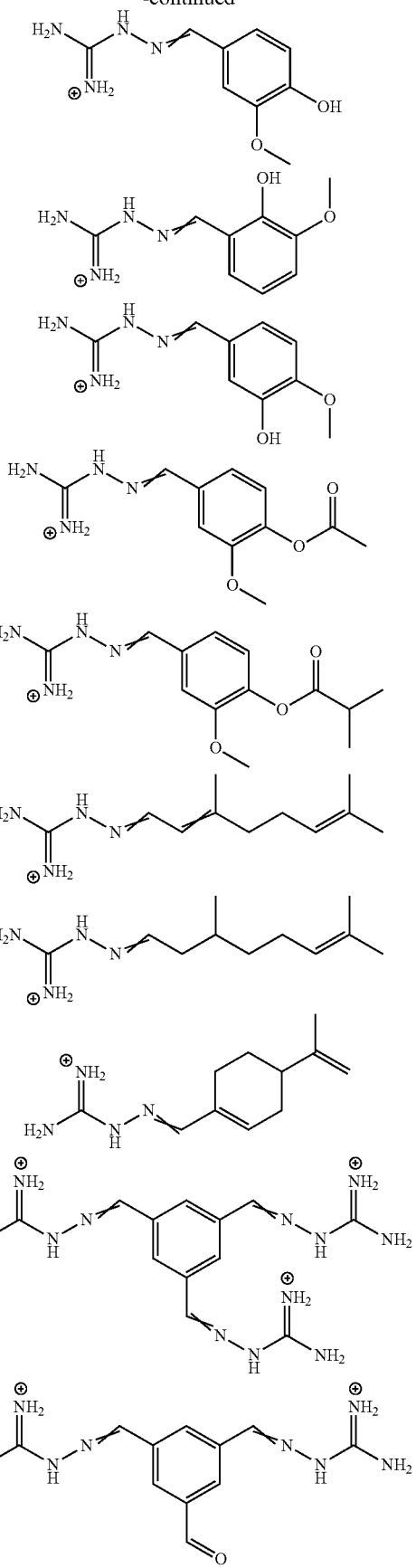

31
-continued
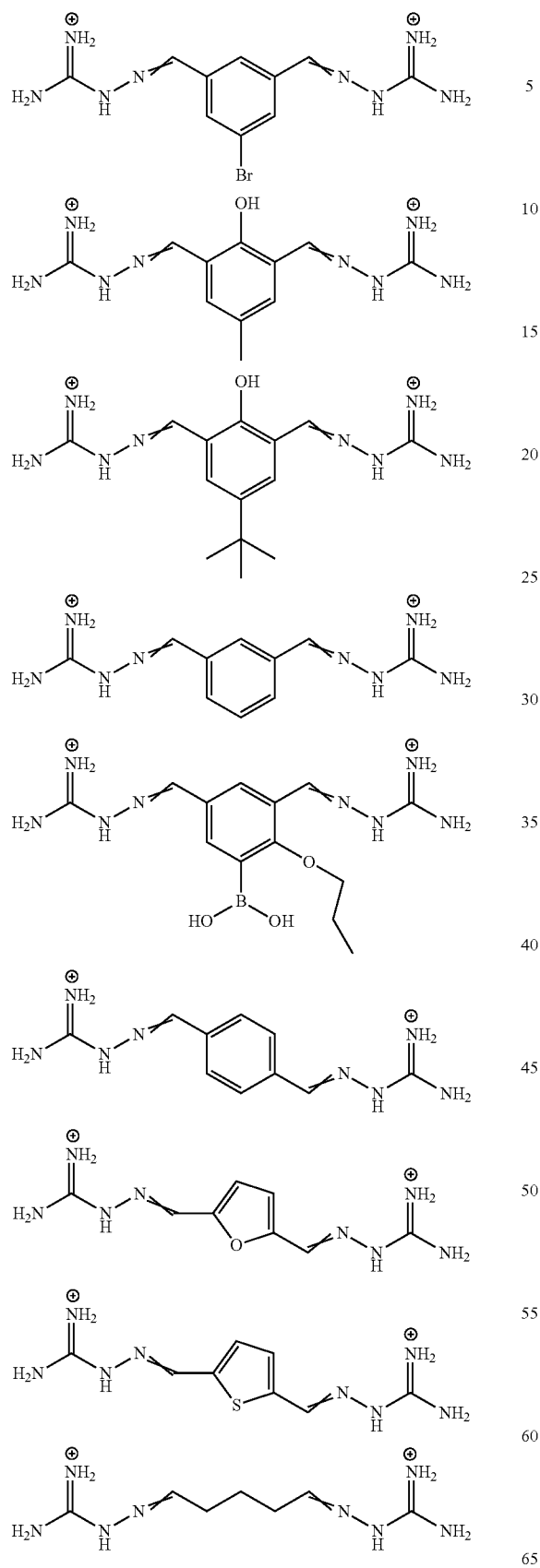
32
-continued
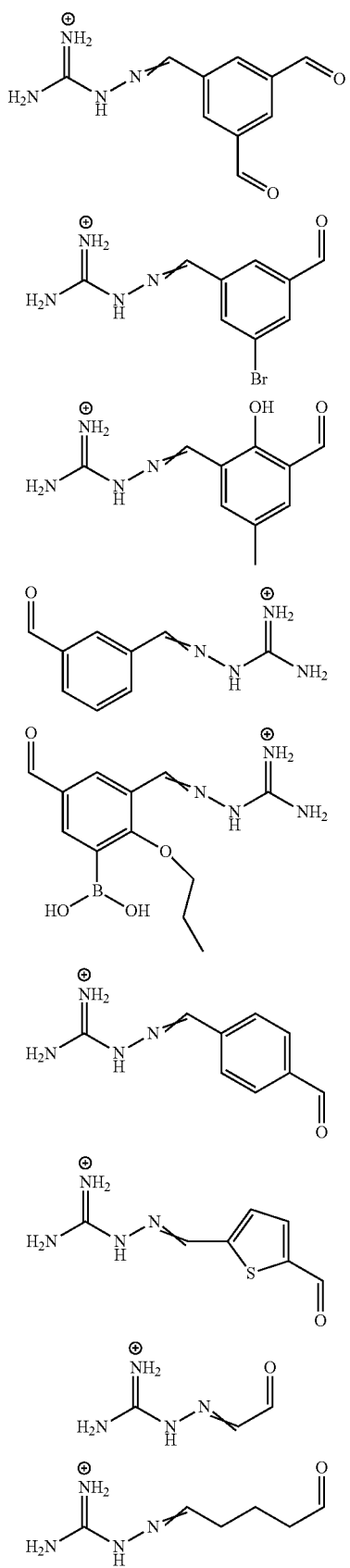

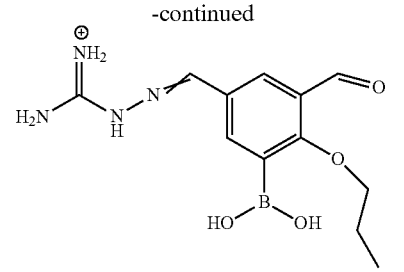
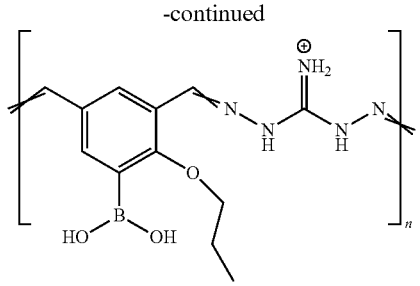
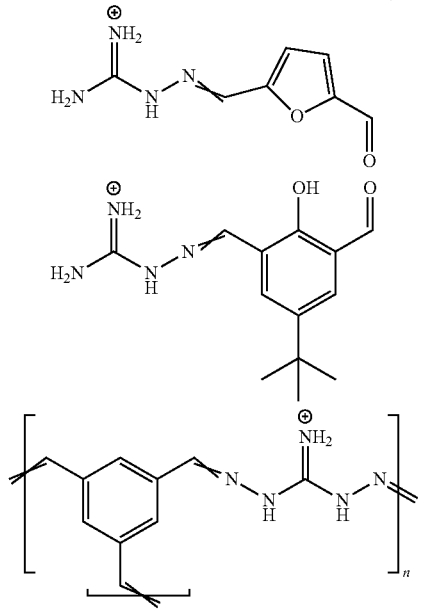
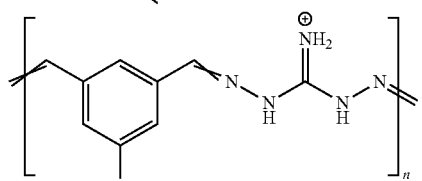
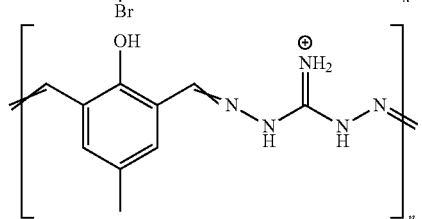
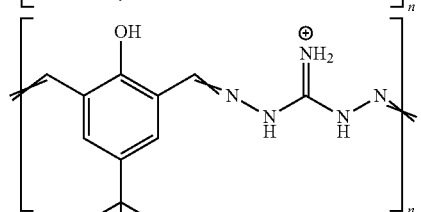
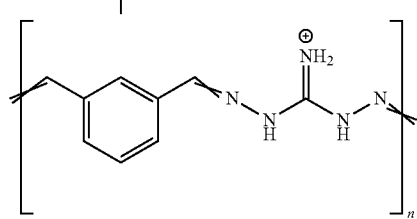
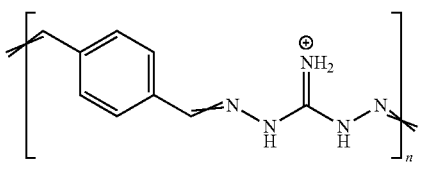
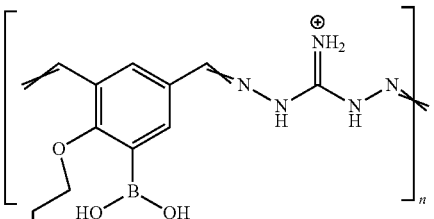
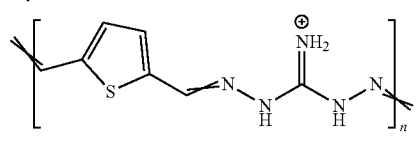
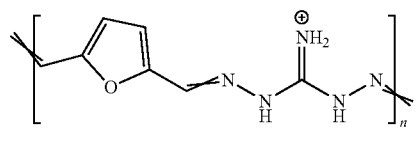
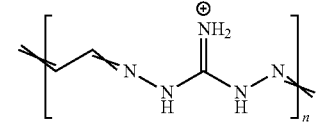
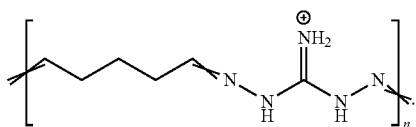
3. The composition of either claim 1 or claim 2, wherein the compound is an active agent.
4. The composition of claim 3, wherein the active agent is formed by self-assembly of a first component molecule and a second component molecule.
5. The composition of claim 3, wherein the active agent has antimicrobial activity.
* * * * *